(12) United States Patent
Gagnon

(10) Patent No.: US 9,920,125 B2
(45) Date of Patent: Mar. 20, 2018

(54) METHODS FOR USE OF MIXED MULTIFUNCTIONAL SURFACES FOR REDUCING AGGREGATE CONTENT IN PROTEIN PREPARATIONS

(71) Applicant: AGENCY FOR SCIENCE, TECHNOLOGY AND RESEARCH, Connexis (SG)

(72) Inventor: Peter Gagnon, Centros (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 44 days.

(21) Appl. No.: 14/555,099

(22) Filed: Nov. 26, 2014

(65) Prior Publication Data

US 2015/0183879 A1    Jul. 2, 2015

Related U.S. Application Data

(63) Continuation of application No. PCT/SG2013/000047, filed on Feb. 6, 2013.
(Continued)

(51) Int. Cl.
*C07K 16/28* (2006.01)
*C07K 14/755* (2006.01)
(Continued)

(52) U.S. Cl.
CPC .......... *C07K 16/2863* (2013.01); *C07K 1/165* (2013.01); *C07K 14/755* (2013.01);
(Continued)

(58) Field of Classification Search
CPC .......................... B01D 15/363; B01D 15/362
See application file for complete search history.

(56) References Cited

U.S. PATENT DOCUMENTS 5,154,822 A * 10/1992 Simpson .................. B01J 20/06
210/198.2
5,283,339 A * 2/1994 Arnold ..................... C07K 1/22
548/104
(Continued)

FOREIGN PATENT DOCUMENTS

CN     1311797     9/2001
CN     1759186     4/2006
(Continued)

OTHER PUBLICATIONS

Gagnon et al., "Antibody Aggregate Removal by Hydroxyapatite Chromatography," Current Pharmaceutical Biotechnology, 2009, 10, 440-446.
(Continued)

*Primary Examiner* — Krishnan S Menon
*Assistant Examiner* — Ryan B Huang
(74) *Attorney, Agent, or Firm* — Pillsbury Winthrop Shaw Pittman LLP

(57) ABSTRACT

Methods for reduction of aggregate levels in antibody and other protein preparations comprising the steps of treatment with an organic multivalent cation (e.g., ethacridine, chlorhexidine, or polyethylenimine) and treatment with a composition having a combination of surfaces bearing electronegative chemical moieties and surfaces bearing electropositive chemical moieties.

83 Claims, 2 Drawing Sheets

Related U.S. Application Data

(60) Provisional application No. 61/653,904, filed on May 31, 2012.

(51) Int. Cl.
    *C07K 16/18* (2006.01)
    *C07K 16/00* (2006.01)
    *C07K 16/06* (2006.01)
    *C07K 16/32* (2006.01)
    *C07K 1/16* (2006.01)

(52) U.S. Cl.
    CPC ............ *C07K 16/00* (2013.01); *C07K 16/065* (2013.01); *C07K 16/18* (2013.01); *C07K 16/32* (2013.01); *C07K 2317/55* (2013.01)

(56) References Cited

U.S. PATENT DOCUMENTS

| | | |
|---|---|---|
| 5,559,250 A | 9/1996 | Cook et al. |
| 7,169,908 B2* | 1/2007 | Lester ............... C12P 21/02 435/69.1 |
| 2004/0024344 A1* | 2/2004 | Trese ............... C12N 9/6435 604/6.04 |
| 2008/0177048 A1* | 7/2008 | Gagnon ............ B01D 15/3847 530/413 |
| 2008/0193981 A1 | 8/2008 | Fahrner et al. |
| 2009/0306342 A1* | 12/2009 | Maeji ............. C01N 33/54393 530/344 |
| 2009/0318674 A1 | 12/2009 | Gagnon |
| 2010/0069617 A1 | 3/2010 | Gagnon |

FOREIGN PATENT DOCUMENTS

| | | |
|---|---|---|
| CN | 102119168 | 7/2011 |
| JP | 2006-517415 A | 7/2006 |
| JP | 2010-517942 | 5/2010 |
| JP | 2013-531623 | 8/2013 |
| JP | 2013-535463 | 9/2013 |
| WO | WO 99/64462 | 12/1999 |
| WO | WO2004/092393 A1 | 10/2004 |
| WO | 2008086335 A2 | 7/2008 |
| WO | WO 2008/086335 | 7/2008 |
| WO | 2009149067 A1 | 12/2009 |
| WO | WO 2011/049798 A1 | 4/2011 |
| WO | WO 2011/146179 | 11/2011 |
| WO | WO2012059495 | 5/2012 |

OTHER PUBLICATIONS

Gagnon, "Monoclonal antibody purification with hydroxyapatite," New Biotechnology, vol. 25, No. 5, Jun. 2009, 287-293.
Gagnon, "IgG Aggregate Removal by Charged-Hydrophobic Mixed Mode Chromatography," Current Pharmaceutical Biotechnology, 2009, 10, 434-439.
Avantor Ion Exchange Chromatography Media: Selection guide for BAKERBOND™ Process Chromatography Media [retrieved on Mar. 12, 2012] Retrieved from the internet: http://web.archive.org/web/20 111128142120;http://www.avantormaterials.com/Phannaceutical/Products/Chromatography-Mediallon-Exchange-Chromatography-Media.aspx published on Nov. 28, 2011 as per Wayback Engine (3 pages).
Matsuzawa et al., "Study on DNA precipitation with a cationic polymer PAC (poly aluminuim chloride)," Nucleic Acids Research Supplement No. 3, (2003) 163-164.
Akcasu et al., "5-Hydroxytryptamine in Cerebrospinal Fluid," Nature vol. 187, Jul. 23, 1960, 324.
Peram et al., "Monoclonal Antibody Purification Using Cationic Polyelectrolytes: An Alternative to Column Chromatography," Biotechnol. Prog., 2010, vol. 26, No. 5, 1322-1331.
Dissing et al., "Integrated removal of nucleic acids and recovery of LDH from homogenate of beef heart by affinity precipitation," Bioseparation 7: 221-229, 1999.
Cordes et al., "Precipitation of Nucleic Acids Poly(ethyleneimine)," Biotechnol. Prog. 1990, 6, 283-285.
Glynn, "Process-scale Precipitation of Impurities in Mammalian Cell Culture Broth," Process Scale Purification of Antiobodies, 2009, 309-324.
Christensen et al., "Simple separation of DNA in antibody purification," Protein Expression and Purifications 37 (2004) 468-471.
Ongkudon et al., "Analysis of Selective Metal-Salt-Induced Endotoxin Precipitation in Plasmid DNA Purification Using Improved Limulus Amoebocyte Lysate Assay and Central Composite Design" Anal. Chem. 2011, 83, 391-397.
Ma et al., "Using precipitation by polyamines as an alternative to chromatographic separation in antibody purification processes," Journal of Chromatography B, 878 (2010) 798-806.
Kejnovsky et al., "DNA extraction by zinc," Nucleic Acids Research, 1997, vol. 25, No. 9, 1870-1871.
Gagnon, "Dissociation of Antibody—Contaminant Complexes With Hydroxyapatite," Winter 2010/2011 BioProcessing Journal, pp. 14-24.
Gagnon et al. "Chromatographic behavior of IgM:DNA complexes," Journal of Chromatography A, 1218 (2011) 2405-2412.
Metchner et al., "The effects of hitchhiker antigens co-eluting with affinity-purified research antibodies," Journal of Chromatography B, 879 (2011) 2583-2594.
Luhrs et al., "Evicting hitchhiker antigens from purified antibodies," Journal of Chromatography B, 877 (2009) 1543-1552.
Shukla et al., "Host Cell Protein Clearance During Protein A Chromatography: Development of an Improved Column Wash Step," Biotechnol. Prog. 2008, 24, 1115-1121.
Extended European Search Report dated Nov. 17, 2015 in corresponding European Patent Application No. 13796628.9 (14 pages).
Chen, Jie et al., "The distinctive separation attributes of mixed-mode resins and their application in monoclonal antibody downstream purification process", Journal of Chromatography A, Sep. 23, 2010, vol. 1217, No. 2, pp. 216-224.
Liu, Hui F. et al., "Exploration of overloaded cation exchange chromatography for monoclonal antibody purification", Journal of Chromatography A, Aug. 12, 2011, vol. 1218, No. 39, pp. 6943-6952.
Brown, Arick et al., "Overloading ion-exchange membranes as a purification step for monoclonal antibodies", Biotechnology and Applied Biochemistry, Jun. 11, 2010, vol. 56, No. 2, pp. 59-70.
Kelley, Brian D. et al., "High-throughput screening of chromatographic separations: IV. Ion-exchange", Biotechnology and Bioengineering, Mar. 20, 2008, vol. 100, No. 5, pp. 950-963.
Pezzini, Jerome et al., "Antibody capture by mixed-mode chromatography: A comprehensive study from determination of optimal purification conditions to identification of contaminating host cell proteins", Journal of Chromatography A, NL, Sep. 17, 2011, vol. 1218, No. 45, pp. 8197-8208.
Pete Gagnon, "Technology trends in antibody purification", Journal of Chromatography A, Oct. 20, 2011, vol. 1221, pp. 57-70.
Japanese Office Action dated Nov. 15, 2016 for Appln. No. 2015-514963.
Gagnon, "Technology trends in antibody purification", Journal of Chromatography A. 1221, 2012, pp. 57-70.
European Office Action dated Jan. 11, 2017 for Appl. No. 13796628.9.
Chinese Office Action dated Aug. 26, 2016 in corresponding Chinese Patent Application No. 201380039329.2 (19 pages).
English translation of Japanese Office Action dated Jun. 27, 2017 for Japanese Patent Application No. 2015-514963.

\* cited by examiner

METHODS FOR USE OF MIXED MULTIFUNCTIONAL SURFACES FOR REDUCING AGGREGATE CONTENT IN PROTEIN PREPARATIONS

CROSS-REFERENCE TO RELATED APPLICATIONS

This application is a continuation of PCT/SG2013/000047 filed Feb. 6, 2013, which claims the priority of U.S. Provisional Application No. 61/653,904, filed May 31, 2012 the disclosures of which are incorporated herein by reference in their entireties.

FIELD OF THE INVENTION

This invention relates to materials for purification of proteins, especially antibodies. It particularly relates to materials for reducing the content of protein aggregates. It further relates to the integration of these capabilities with other purification methods to achieve desired levels of final purification of a protein.

BACKGROUND OF THE INVENTION

It has been indicated that unnatural hetero-aggregates form spontaneously between host cell-derived contaminants and recombinant proteins produced by in vitro cell culture methods (Shukla et al., Biotechnol. Progr. (2008) 24:1115-1121; Luhrs et al., J. Chromatogr. B (2009) 877:1543-1552; Mechetner et al., J. Chromatogr. B (2011) 879:2583-2594; Gagnon et al., J. Chromatogr. A, (2011) 1218:2405-2412; Gagnon, Bioprocessing J. (2010) 9(4):14-24). These hetero-aggregates may be considered unnatural in two respects: 1) constituent contaminants are often of non-human origin, secreted by living non-human host cells or released into the culture media when non-human host cells lyse upon death. In living humans, such non-human contaminants do not exist; and 2) constituent contaminants accumulate to high concentrations in comparison to human in vivo systems where dead cell constituents are quickly eliminated. Accordingly, recombinant products are exposed to high levels of strongly interactive contaminants at concentrations that typically do not occur in living systems. Meanwhile, high expression levels of recombinant proteins make them suitable substrates for non-specific associations with these non-human contaminants, favoring the formation of undesirable hetero-aggregates of diverse composition.

The contaminating protein content of hetero-aggregates has been addressed to some extent via direct targeting of the contaminating protein (Shukla et al. and Gagnon et al. supra), as well as indirectly via targeting of the corresponding DNA component responsible for the contaminating protein (Luhrs et al. and Gagnon supra). A reduction of antibody aggregate level has been indicated when some complexes are dissociated (Shukla et al., Mechetner et al., and Gagnon supra). The ability of anion exchangers to reduce levels of antibody-contaminant complexes has been disclosed (Luhrs et al. and Gagnon et al. supra), but an anion exchange treatment that was able to fully eliminate hetero-aggregates has not been indicated. Size exclusion, cation exchange, and hydrophobic interaction chromatography have also been employed in attempts to reduce hetero-aggregates, but these techniques were generally inferior to anion exchange (Gagnon et al. supra).

The specific source of contaminants that form stable associations with antibodies is not always known (see, for example, Shukla et al. supra). Some efforts have focused on DNA contaminants with little attention to the specific source of other possible contaminants (Gagnon et al. and Gagnon supra). Some efforts indicating an association of host contaminants with aggregates in antibody preparation have focused specifically on contaminants comprising chromatin catabolites (Luhrs et al. and Mechetner et al. supra). In these examples, aggregation may be mediated directly through the immunospecificity of the antibody for chromatin catabolites such as histones and DNA. It has been indicated that chromatin catabolites are also capable of forming stable complexes with antibodies via non-specific interactions. Thus, monoclonal antibodies with known immunospecificities for antigens not including chromatin catabolites, can form highly stable aggregates of diverse descriptions with nucleosomes, histones, and DNA derived from the nuclei of dead host cells. It has been particularly indicated that chromatin catabolites are highly represented in high molecular weight (HMW) aggregates. HMW aggregates are of particular concern because of their suspected involvement in promoting the formation of therapy-neutralizing antibodies. HMW aggregates are generally defined as aggregates of a size greater than small multiples of the antibody of interest. For example, 2-antibody associations are not considered HMW aggregates, nor are most 4-antibody aggregates. However, aggregates of much greater size, such as corresponding to about 8 to about 10 or more antibodies may be generally classified as HMW aggregates.

Treating antibody preparations with agents that might be expected to dissociate hetero-aggregates has generally proven ineffective. For example, employing high concentrations of urea, salts, or combinations of the two does not substantially dissociate IgM-contaminant hetero-aggregates (Gagnon et al. supra). Protein A affinity chromatography with pre-elution washes of urea, alcohol, and surfactants has been indicated to reduce hetero-aggregate levels more effectively than without washes (Shukla et al. supra), as did pre-elution washes combining urea, salt, and EDTA with protein G affinity chromatography (Mechetner et al. supra). Anion exchange chromatography with a pre-elution wash of urea has been indicated to reduce hetero-aggregates more effectively than in the absence of a urea wash (Gagnon et al. supra). Cation exchange chromatography has also been indicated to reduce hetero-aggregates more effectively with a pre-elution EDTA wash than without the wash (Gagnon et al. supra). Finally, hydroxyapatite with pre-elution washes of urea and/or salt have also reduced hetero-aggregates more effectively than without such washes (Gagnon supra). Despite these observations, in general, the use of dissociating agents in pre-elution washes of antibodies bound to chromatography columns has been only moderately successful.

Organic multivalent cations have been indicated for the precipitation of acidic proteins (Farhner et al., U.S. Patent Application No. 20080193981; Ma et al., J. Chromatogr. B (2010) 878:798-806; Peram et al., Biotechnol. Progr., (2010) 26:1322-1326; Glynn, in U. Gottschalk (ed.), Process Scale Purification of Antibodies, J. T. Wiley and Sons, (2009) Hoboken, 309-324), as well as for precipitation of DNA and endotoxins (Glynn supra; Cordes et al., Biotechnol. Progr., (1990) 6:283-285; Dissing et al., Bioseparation, (1999) 7 221:9-11) and inactivation of virus (Bernhardt, U.S. Pat. No. 5,559,250). Multivalent metal cations have also been indicated to remove DNA and endotoxin from some protein preparations (Akcasu et al., Nature, (1960) 187:323-324; Matsuzawa et al., Nucl. Acids Res., (2003) 3(3):163-164; Christensen et al., Prot. Expr. Purif., (2004)

37:468-471; Kejnovsky et al., *Nucl. Acids Res.*, (1997) 25:1870-1871; Ongkudon et al., *Anal. Chem.*, (2011) 83 391:13-17).

SUMMARY OF THE INVENTION

In certain embodiments, the invention provides methods for reducing the aggregate content of a sample such as a protein preparation containing a desired protein; certain methods include the steps of: (i) providing a first component which is a first solid substrate having an electronegative surface: (ii) providing a second component which is a second solid substrate having an electropositive surface; (iii) contacting the sample with the first and second components, where the first and second components are configured such that the sample may contact both components simultaneously under operating conditions that substantially prevent binding of the desired protein to the first or second component; and (iv) separating a resulting sample containing the desired protein with a reduced aggregate content from the first and second components.

DETAILED DESCRIPTION OF THE INVENTION

Figure 1:
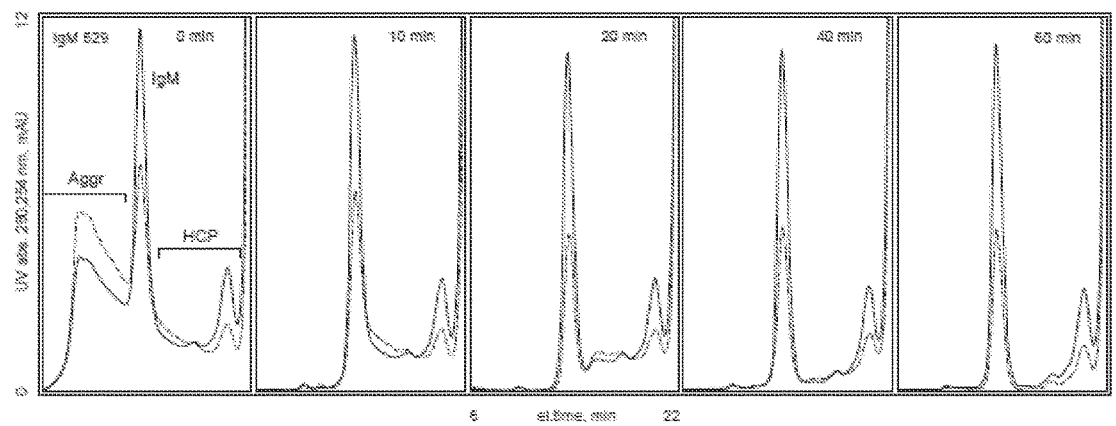
FIG. 1 shows a time course plot of the size exchange chromatography (SEC) profiles sampled at indicated intervals in the purification of IgM-529 which was subjected to allantoin-ethacridine batch particle treatment. Aggr: aggregate. HCP: host cell protein. Solid line: 280 nm. Broken line: 254 nm. All time scales same as center panel.

It has been surprisingly discovered that in certain embodiments of the invention a composition of matter comprising a combination of a solid material with an electronegative surface and a solid material with an electropositive surface is more effectively able to reduce the content of high molecular weight (HMW) aggregates and hetero-aggregates in protein preparations than materials relying solely on anion exchangers or cation exchangers. In certain embodiments, the compositions particularly reduce the content of aggregates that include chromatin remnants, such as nucleosomes, and/or histones, and/or DNA. In certain embodiments, the invention has the additional ability to remove agents such as multivalent ions and antiviral compounds that may have been added to the protein preparation.

It has been surprisingly discovered that in certain embodiments of the invention aggregate levels in protein preparations can be dramatically reduced by the combined addition to such preparations of soluble multivalent cations of mixed chemical character and the subsequent addition of insoluble particles or other substrates of mixed chemical character. Experimental results demonstrate that this treatment permits dramatically greater reduction of high molecular weight (HMW) aggregate content and dissociation of hetero-aggregates than liquid phase treatments with salts and/or chaotropes, single-mechanism solid phase methods, or combinations of a solid phase method with an intended aggregate-dissociating wash. A valuable benefit of this approach is that the soluble agents are themselves removed from the protein preparation, yielding a substantially aggregate-free protein preparation, also substantially free of multivalent cations. This can surprisingly occur within a period of an hour or less even when the multivalent cations and insoluble particles are present in extremely low amounts such as about 0.02 to about 0.025% and about 2 to about 5%, respectively. Experimental evidence further demonstrates that in certain embodiments of the invention, sample treatment in advance with the organic multivalent cations enhances the results achieved by a combination of electronegative and electropositive particles.

In certain embodiments, the invention provides methods for reducing aggregate content of recombinant protein preparations, particularly including antibodies, clotting factors such as Factor VIII, and recombinant proteins. Without being bound to any specific theory, it has been unexpectedly discovered that aggregates are stabilized by interactions with foreign substances. Contacting an antibody preparation with multifunctional surfaces that have higher affinity for the foreign substances than the antibody have the effect of displacing the foreign substances, which can then be removed by simple removal of the multifunctional surfaces to which they are bound. In certain embodiments, aggregate levels are reduced substantially, and antibody recovery sometimes increases over the amount believed to be present, indicating the ability of the method to dissociate aggregates and restore the dissociated antibody to the purifiable product population. In certain embodiments, the method can also dissociate complexes of single antibodies with contaminants. In addition to producing antibody preparations with lower aggregate populations, in certain embodiments, the treated antibodies also exhibit lower host protein, DNA, endotoxin, and virus contamination.

In certain embodiments, the methods of the invention involve simultaneously contacting a sample containing a desired antibody with at least two kinds of surfaces, one dominantly electronegative and the other dominantly electropositive. Either surface may embody additional chemical functionalities. Additional chemical functionalities may include hydrophobic, pi-pi bonding, hydrogen bonding, or metal affinity functionalities, among others. In certain embodiments, the electronegative surfaces and electropositive surfaces provide different degrees of utility, apparently indicating that they individually favor interactions with different subsets of foreign substances. This feature of certain embodiments has been further demonstrated by the observation that the electronegative surfaces and electropositive surfaces are more effective when applied together than individually.

In certain embodiments, the surfaces may include porous or non-porous particles dispersed throughout the protein preparation, or packed in a column, or initially dispersed and then packed in a column.

In certain embodiments, aggregate removal can be enhanced by pretreating the sample with soluble organic multivalent cations, alone or in combination with other agents, in which case the method has the additional utility of removing the organic multivalent cations, and potentially the other agents. Utility of the method may be otherwise enhanced by inclusion of antiviral agents, alone or in the presence of multivalent cations.

In certain embodiments, the invention provides methods for reducing the aggregate content of a sample such as a protein preparation containing a desired protein; certain methods include the steps of: (i) providing a first component which is a first solid substrate having an electronegative surface: (ii) providing a second component which is a second solid substrate having an electropositive surface; (iii) contacting the sample with the first and second components, where the first and second components are configured such that the sample may contact both components simultaneously under operating conditions that substantially prevent binding of the desired protein to the first or second component; and (iv) separating a resulting sample containing the desired protein with a reduced aggregate content from the first and second components.

In some embodiments, the first and second components are combined prior to contacting the sample.

In some embodiments, the first and second components may be combined with additional components that bear charged or uncharged chemical surfaces and which may bear additional chemical moieties capable of participating in hydrogen boding, hydrophobic interactions, metal affinity or other intermolecular interactions with components of the sample In one or more of the preceding embodiments, the sample is contacted with a soluble organic multivalent cation of mixed chemical character prior to contacting the first substrate having an electronegative surface In one or more of the preceding embodiments, the sample is incubated with the soluble organic multivalent cation of mixed chemical character for an appropriate period of time prior to contacting the first and second components.

In one or more of the preceding embodiments, the sample is incubated with the first and second components for an appropriate period of time.

In one or more of the preceding embodiments, the organic multivalent cation having mixed chemical character is removed from the sample in the step of separating the sample with a reduced aggregate content from the first and second components. In certain embodiments organic multivalent cation having mixed chemical character is removed from the sample in the step of separating the sample with a reduced aggregate content from the first and second components to the extent that the organic multivalent cation having mixed chemical character is associated with a substrate of the first or second component or an additional component other than the first and second component which third component is in combination with the first and second components in contact with the sample. For example, such third component may be a material bearing a hydrophobic functionality.

In one or more of the preceding embodiments, the first substrate is particulate.

In one or more of the preceding embodiments, the second substrate is particulate.

In one or more of the preceding embodiments, the particulate substrate or substrates is each provided as a plurality of particles.

In one or more of the preceding embodiments, the particles of the first substrate, the second substrate or both are non-porous.

In one or more of the preceding embodiments, the particles of the first substrate, the second substrate or both are porous.

In one or more of the preceding embodiments, the pore size of the porous particles is large enough to permit entry of a protein in a protein preparation.

In one or more of the preceding embodiments, the pore size of the porous particles is too small to permit entry of a protein in a protein preparation.

In one or more of the preceding embodiments, the average pore size of the porous particles is between about 10 nm and about 100 nm.

In one or more of the preceding embodiments, the particles are sandwiched between porous membranes or monoliths.

In one or more of the preceding embodiments, the particles are sandwiched between woven or amorphous fibrous filters.

In one or more of the preceding embodiments, the particles are sandwiched between crystalline frits.

In one or more of the preceding embodiments, the particles are embedded in a reticular polymer network.

In certain embodiments, the first and or second and or other components/substrates are non-particulate. In certain such embodiments the solid substrate of the first and or second component is independently a fiber, a hollow-fiber, a membrane, or a monolith.

In one or more of the preceding embodiments, the operating conditions are of a nature which substantially prevents the binding of the desired protein to the first and second components. In certain of such embodiments, the operating conditions additionally prevent substantial loss of the desired protein through interactions with either the first or second components, or other substrates. Such conditions may include a conductivity value sufficiently high to suspend strong charge interactions between the desired protein and first and second components. Such conditions may also suspend strong charge interactions between the desired protein and multivalent cations or particles. Such operating conditions may include the presence of other additives contacting the sample in addition to the first and second components to modulate other types of chemical interactions between the desired protein and the first or second components.

In one or more of the preceding embodiments, the conductivity of the sample is at a sufficiently high level to substantially avoid precipitation of the desired protein from the sample while contacting the soluble organic multivalent cation of mixed chemical character.

In one or more embodiments, methods of the invention exhibit an ability to tolerate high salt concentration as may be measured by conductivity. For example, in some embodiments, a sample may be purified with an eluent having a conductivity of about 15 mS/cm. In one or more embodiments, conductivity may be at least 13 mS/cm. In some embodiments, the conductivity may be lower for some proteins with the proviso that the salt concentration is sufficient to prevent desired-protein from binding to the first and second components. Thus, in some embodiments, a conductivity may be as low as about 5 to about 10 mS/cm.

In one or more of the preceding embodiments, the conductivity of the sample is greater than 20 mS/cm.

In one or more of the preceding embodiments, the conductivity of the sample is greater than 30 mS/cm.

In one or more of the preceding embodiments, the conductivity of the sample is greater than about 40 mS/cm.

In one or more of the preceding embodiments, the conductivity of the sample is greater than about 100 mS/cm.

In one or more of the preceding embodiments, the conductivity of the sample is at least 5%, 10%, 20%, 50%, 100% or 200% higher than the conductivity sufficient to substantially avoid precipitation of the desired protein from the sample while contacting the soluble organic multivalent cation of mixed chemical character. In one or more of the preceding embodiments, the conductivity of the sample is at least 5%, 10%, 20%, 50%, 100% or 200% higher than the conductivity sufficient to substantially avoid binding of the desired protein with the first or second components.

In one or more of the preceding embodiments, the aggregates comprise homo-aggregates of the desired protein.

In one or more of the preceding embodiments, the presence of homo-aggregates of the desired protein is substantially eliminated.

In one or more of the preceding embodiments, the aggregates comprise hetero-aggregates of the desired protein and a contaminant.

In one or more of the preceding embodiments, the hetero-aggregates are of substantially the same hydrodynamic size as the desired protein.

In one or more of the preceding embodiments, a contaminant may be a nucleic acid, nucleotide, endotoxin, metal ion, protein, lipid, or cell culture media component.

In one or more of the preceding embodiments, the presence of hetero-aggregates of the desired protein and a contaminant is substantially eliminated.

In one or more of the preceding embodiments, the desired protein is an antibody or antibody fragment or a conjugate of an antibody or antibody fragment. In certain embodiments the antibody is an IgG, IgM, IgD, IgE, or IgA. In certain embodiments the antibody fragment is a Fc-fusion protein or an immunoconjugate.

In one or more of the preceding embodiments, the desired protein is a recombinant protein.

In one or more of the preceding embodiments, the desired protein is a clotting factor.

In one or more of the preceding embodiments, the clotting factor is Factor VIII.

In one or more of the preceding embodiments, the desired protein is a growth hormone. In some such embodiments the growth hormone is a human growth hormone.

In one or more of the preceding embodiments, the sample is a cell culture harvest, a cell culture supernatant, an antibody-containing solution derived from a cell culture, or an antibody-containing solution from a previous stage of protein purification. In some such embodiments, the cultured cells are mammalian cells. In some such embodiment, the cultured cells are bacterial cells. In some such embodiments, the cultured cells are yeast cells.

In one or more of the preceding embodiments, the sample is an antibody-containing solution from a previous stage of protein purification.

In one or more of the preceding embodiments, the sample is an eluate from a chromatography column.

In one or more of the preceding embodiments, the sample may be unpurified, at an intermediate level of purity, or highly purified.

In one or more of the preceding embodiments, the sample is contacted with the first and second components by flowing the preparation through the first and second components.

In one or more of the preceding embodiments, the electronegativity of the surface of the first component is conferred through one or more kinds of complex chemical moieties that embody more than one chemical functionality, or through a combination of simple and complex chemical groups mixed on the surface, or a combination of surfaces of differing chemical composition.

In one or more of the preceding embodiments, the electronegativity of the surface of the first component is conferred in part by a moiety from the group consisting of iminodiacetic acid, ethylene glycol(aminoethylether)diacetic acid, nitriloacetic acid, aspartic acid, glutamic acid, a carboxylic acid, sulfurous acid, sulfonate, and phosphoric acid.

In one or more of the preceding embodiments, the electropositivity of the surface of the second component is conferred through one or more kinds of complex chemical groups that embody more than one chemical functionality, or through a combination of simple and complex chemical groups mixed on the surface, or a combination of surfaces of differing chemical composition.

In one or more of the preceding embodiments, the surfaces of additional solid components/substrates may bear additional electropositive, and or electronegative, and/or uncharged chemical groups, such as may be capable of participating in hydrogen bonding, hydrophobic interactions, metal affinity, or other chemical interactions. In particular embodiments, metal affinity may comprise affinity for metal ions, zero valent metals, or combinations thereof.

In one or more of the preceding embodiments, the electropositivity of the surface of the second component is conferred in part by a moiety selected from the group consisting of tris(2-aminoethyl)amine, diethylenetriamine, triethylenetetramine, tetraethylenepentamine, polypropylenimine tetramine, PAMAM dendrimer (ethylenediamine core), deferoxamine, a primary amino group, a secondary amino group, a tertiary amino group, a quaternary amino group and combinations thereof.

In one or more of the preceding embodiments, the electronegativity of the surface of the first component is conferred in part by iminodiacetic acid and the electropositivity of the surface of the second component is conferred in part by tris(2-aminoethyl)amine.

In one or more of the preceding embodiments, the first component has a surface-bound chemical moiety possessing metal affinity functionality.

In one or more of the preceding embodiments, the electropositive surface of the second component includes a surface-bound chemical moiety possessing metal affinity functionality.

In one or more of the preceding embodiments, at least one of the substrates has one or more chemical moieties in addition to the surface-bound chemical moiety possessing metal affinity functionality wherein such additional chemical moieties enhance the capacity of one or more of the components to participate in hydrogen bonding, hydrophobic interactions, or pi-pi binding with a protein of the protein preparation.

In one or more of the preceding embodiments, the surface-bound chemical moiety possessing metal affinity functionality is a multidentate metal chelating moiety.

In one or more of the preceding embodiments, the organic multivalent cation of mixed chemical character is selected from the group consisting of ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), polyethyleneimine, chlorhexidine, and poly-amino acids.

In one or more of the preceding embodiments, the organic multivalent cation of mixed chemical character is ethacridine, polyethylenimine or chlorhexidine or a salt thereof.

In one or more of the preceding embodiments, the organic multivalent cation of mixed chemical character is ethacridine or a salt thereof.

In one or more of the preceding embodiments, wherein the organic multivalent cation of mixed chemical character is present in an amount between approximately 0.01% and approximately 0.05%.

In one or more of the preceding embodiments, the organic multivalent cation of mixed chemical character is present in an amount less than approximately 0.01%.

In one or more of the preceding embodiments, the organic multivalent cation of mixed chemical character is present in an amount less than approximately 0.005%.

In one or more of the preceding embodiments, the organic multivalent cation of mixed chemical character is present in an amount less than approximately 0.001%.

In one or more of the preceding embodiments, the organic multivalent cation of mixed chemical character is present in an amount between approximately 0.020 and approximately 0.025%.

In one or more of the preceding embodiments, the sample is treated with more than one organic multivalent cation from the group consisting of polyethyleneimine, polyallyamine, ethacridine, and chlorhexidine and salts thereof prior to the step of contacting the sample with the first and second components.

In one or more of the preceding embodiments, the organic multivalent cations used to treat the sample prior to the step of contacting the sample with the first and second components are provided in a concentration of less than 1% or in a concentration of less than 0.1%.

In one or more of the preceding embodiments, the organic multivalent cations used to treat the sample prior to the step of contacting the sample with the first and second components are provided in a concentration between approximately 0.01% and approximately 0.05%.

In one or more of the preceding embodiments, the organic multivalent cations used to treat the sample prior to the step of contacting the sample with the first and second components are provided in a concentration less than approximately 0.01%.

In one or more of the preceding embodiments, the organic multivalent cations used to treat the sample prior to the step of contacting the sample with the first and second components are provided in a concentration less than approximately 0.005%.

In one or more of the preceding embodiments, the organic multivalent cations used to treat the sample prior to the step of contacting the sample with the first and second components are provided in a concentration less than approximately 0.001%.

In one or more of the preceding embodiments, the organic multivalent cations used to treat the sample prior to the step of contacting the sample with the first and second components are provided in a concentration between approximately 0.020 and approximately 0.025%.

In one or more of the preceding embodiments, the sample is additionally contacted with a soluble organic modulator selected from the group consisting of nonionic organic polymers, organic solvents, surfactants, and ureides, prior to the step of contacting the sample with the first and second components.

In one or more of the preceding embodiments, the sample is additionally contacted with an antiviral agent, prior to the step of contacting the sample with the first and second components.

In one or more of the preceding embodiments, the antiviral agent is a non-multivalent organic cation.

In one or more of the preceding embodiments, the antiviral agent is selected from the group consisting of benzalkonium chloride, methylene blue and tri (n-butyl) phosphate.

In one or more of the preceding embodiments, the antiviral agent is present in an amount less than approximately 1% (w/v).

In one or more of the preceding embodiments, the antiviral agent is present in an amount less than approximately 0.1% (w/v).

In one or more of the preceding embodiments, the antiviral agent is present in an amount less than approximately 0.01% (w/v).

In one or more of the preceding embodiments, the antiviral agent is present in an amount less than approximately 0.001% (w/v).

In one or more of the preceding embodiments, methods comprise the additional steps of, prior to the step of contacting the sample with the first and second components, contacting the sample with a ureide in an amount sufficient for the ureide to be supersaturated in the protein preparation, and separating the supernatant containing the desired protein from the solid or undissolved portions of the sample.

In one or more of the preceding embodiments, the step of contacting the sample with the ureide occurs prior to the step of contacting the sample with the soluble organic multivalent cation of mixed chemical character.

In one or more of the preceding embodiments, the step of contacting the sample with the ureide occurs substantially simultaneously with the step of contacting the sample with the soluble organic multivalent cation of mixed chemical character.

In one or more of the preceding embodiments, the step of contacting the sample with the ureide occurs after the step of contacting the sample with the soluble organic multivalent cation of mixed chemical character.

In one or more of the preceding embodiments, the ureide is selected from the group consisting of urea, uric acid, hydantoin, allantoin, alcloxa, aldioxa, hemocane, ureidohydantoin, 5-ureidohydantoin, glyoxylureide, glyoxylic acid diureide, 2,5-dioxo-4-imidazolidinyl urea, and purines.

In one or more of the preceding embodiments, the ureide is allantoin.

In one or more of the preceding embodiments, the ureide is uric acid.

In one or more of the preceding embodiments, the allantoin is present in an amount greater than 0.5% (w/v).

In one or more of the preceding embodiments, the allantoin is present in an amount greater than approximately 1% (w/v) or in an amount greater than approximately 2% (w/v) or in an amount greater than approximately 5% (w/v) or in an amount greater than approximately 10% (w/v).

In one or more of the preceding embodiments, the uric acid is present in an amount greater than 0.0025% (w/v).

In one or more of the preceding embodiments, the uric acid is present in an amount greater than approximately 0.01% (w/v).

In one or more of the preceding embodiments, the uric acid is present in an amount greater than approximately 0.1% (w/v).

In one or more of the preceding embodiments, the uric acid is present in an amount greater than approximately 1% (w/v).

In one or more of the preceding embodiments, the step of contacting the sample with the organic modulator occurs prior to the step of contacting the sample with the soluble organic multivalent cation of mixed chemical character.

In one or more of the preceding embodiments, the step of contacting the sample with the organic modulator occurs substantially simultaneously with the step of contacting the sample with the soluble organic multivalent cation of mixed chemical character.

In one or more of the preceding embodiments, the step of contacting the sample with the organic modulator occurs after the step of contacting the sample with the soluble organic multivalent cation of mixed chemical character.

In one or more of the preceding embodiments, the organic modulator is a nonionic organic polymer selected from the group consisting of glycerol, polyethylene glycol, polypropylene glycol and polybutylene glycol.

In one or more of the preceding embodiments, the nonionic organic polymer has an average molecular weight of approximately 500 D or less.

In one or more of the preceding embodiments, the organic modulator is an organic solvent selected from the group consisting of ethylene glycol, propylene glycol, butylene glycol, dimethylsulfoxide, ethanol, isopropanol, and phenoxyethanol.

In one or more of the preceding embodiments, the organic modulator is provided at a concentration of approximately 1% (w/v) or greater. In one or more of the preceding embodiments, where the organic modulator is ethanol or isopropanol, the organic modulator is provided at a concentration of approximately 1% (w/v) or less.

In one or more of the preceding embodiments, the organic modulator is a surfactant selected from the group consisting of Tween, triton, CHAPS, CHAPSO and octyl glucoside.

In one or more of the preceding embodiments, the surfactant is provided at a concentration of approximately 1% (w/v) or less.

In one or more of the preceding embodiments, the surfactant is provided at a concentration of approximately 0.1% (w/v) or less.

In one or more of the preceding embodiments, the organic modulator is a ureide provided in a subsaturating amount.

In one or more of the preceding embodiments, the ureide is selected from the group consisting of urea, hydantoin, and allantoin.

In some embodiments, the present invention provides a kit for the convenient practice of a method of any of preceding embodiments.

In certain embodiments, the invention provides methods for reducing the aggregate content of a sample containing a desired protein; certain methods include the steps of: (i) providing a first component which is a first substrate having an electronegative surface: (ii) providing a second component which is a second substrate having an electropositive surface; (iii) contacting the sample with the first and second components, where the first and second components are configured such that at least some of the aggregates in the sample may contact both components simultaneously; and (iv) separating the sample containing the desired protein with a reduced aggregate content from the first and second components.

In certain embodiments, an organic multivalent cation of mixed chemical character is combined with the sample prior to contacting the sample with the first and second components. In certain embodiments, the first and second components are combined prior to contacting the protein preparation. In certain embodiments, the sample is incubated with the organic multivalent cation of mixed chemical character for an appropriate period of time prior to contacting the sample with the first and second components. In certain embodiments, the sample is incubated with the first and second components for an appropriate period of time. In certain embodiments, the organic multivalent cation having mixed chemical character is removed from the sample in the step of separating the sample with a reduced aggregate content from the first and second components to the extent that the organic multivalent cation having mixed chemical character is associated with a substrate of the first or second component.

In certain embodiments, the first substrate is particulate. In certain embodiments, the second substrate is particulate. The particulate substrate or substrates can each be provided as a plurality of particles. In certain embodiments, either or both of the particles of the first substrate and the second substrate can be non-porous or porous. Such porous particles can have average pore sizes which are large enough to permit entry of a protein in a protein preparation, or too small to permit entry of a protein in a protein preparation, or between about 10 nm and about 100 nm. In certain embodiments where the substrates are particles, the particles are sandwiched between porous membranes or monoliths. In certain embodiments, the particles are sandwiched between woven or amorphous fibrous filters. In certain embodiments, the particles are sandwiched between crystalline frits. In certain embodiments, the particles are embedded in a reticular polymer network.

In certain embodiments, the conductivity of the sample is at a sufficiently high level to substantially avoid precipitation of the desired protein from the sample while contacting the first and second substrates. In certain embodiments, the conductivity of the sample is greater than 20 mS/cm. In others, the sample is greater than 30 mS/cm, greater than about 40 mS/cm, or greater than about 100 mS/cm. In certain embodiments, the conductivity of the sample is at least 5%, 10%, 20%, 50%, 100% or 200% higher than the conductivity sufficient to substantially avoid precipitation of the desired protein from the sample while contacting the organic multivalent cation of mixed chemical character prior to the step of contacting the sample with the first and second components.

In certain embodiments, the aggregates comprise homo-aggregates of the desired protein. In certain such embodiments, the presence of homo-aggregates of the desired protein is substantially eliminated. In certain embodiments, the aggregates comprise hetero-aggregates of the desired protein and a contaminant or multiple contaminants. In certain such embodiments, the hetero-aggregates are of substantially the same hydrodynamic size as the desired protein. In certain embodiments, the contaminant is a nucleic acid, nucleotide, endotoxin, metal ion, protein, lipid, or cell culture media component. In certain such embodiments, the presence of hetero-aggregates of the desired protein and a contaminant is substantially eliminated. In certain embodiments, the aggregates in the sample include both homo-aggregates and hetero-aggregates. In certain embodiments, the desired protein is an antibody or antibody fragment. In certain such embodiments, the sample is a protein preparation such as a cell culture harvest, a cell culture supernatant, an antibody-containing solution derived from a cell culture, or an antibody-containing solution from a previous stage of protein purification. In certain such embodiments, the protein preparation is an antibody-containing solution from a previous stage of protein purification. In certain such embodiments, the protein preparation is an eluate from a chromatography column.

In certain embodiments, the protein preparation may be unpurified, at an intermediate level of purity, or highly purified. In some embodiments, an intermediate level of purity of the sample may be in a range of from about 40% to about 90% purity. In some embodiments, the high level of purity of the sample may be in a range of from about 90% or greater.

In certain embodiments, the protein preparation is contacted with the first and second components by flowing the preparation through the first and second components.

In certain embodiments, the electronegativity of the surface of the first component is conferred through one or more kinds of complex chemical moieties that embody more than one chemical functionality, or through a combination of simple and complex chemical groups mixed on the surface, or a combination of surfaces of differing chemical composition. In certain embodiments, the electronegativity of the surface of the first component is conferred in part by a moiety from the group consisting of iminodiacetic acid, ethylene glycol(aminoethylether)diacetic acid, nitriloacetic acid, aspartic acid, glutamic acid, a carboxylic acid, sulfurous acid, sulfonate, or phosphoric acid. In certain embodiments, the electropositivity of the surface of the second component is conferred through one or more kinds of complex chemical groups that embody more than one chemical functionality, or through a combination of simple and complex chemical groups mixed on the surface, or a combination of surfaces of differing chemical composition. In certain such embodiments, the electropositivity of the surface of the second component is conferred in part by a moiety selected from the group consisting of tris(2-aminoethyl)amine, diethylenetriamine, triethylenetetramine, tetraethylenepentamine, polypropylenimine tetramine, PAMAM dendrimer (ethylenediamine core), deferoxamine, a primary amino group, a secondary amino group, a tertiary amino group, and a quaternary amino group. In certain embodiments, the electronegativity of the surface of the first component is conferred in part by iminodiacetic acid and the electropositivity of the surface of the second component is conferred in part by a moiety from the group consisting of tris(2-aminoethyl)amine. In certain embodiments, the first component has a surface-bound chemical moiety possessing metal affinity functionality and the second component is a second substrate having an electropositive surface. In certain embodiments, the second component is a second substrate having an electropositive surface and the electropositive surface includes a surface-bound chemical moiety possessing metal affinity functionality. In certain such embodiments, at least one of the substrates has one or more chemical moieties in addition to the surface-bound chemical moiety possessing metal affinity functionality wherein such additional chemical moieties enhance the capacity of one or more of the components to participate in hydrogen bonding, hydrophobic interactions, or pi-pi binding with a protein of the protein preparation. In certain embodiments, the surface-bound chemical moiety possessing metal affinity functionality is a multidentate metal chelating moiety.

In certain embodiments, the sample is treated with an organic multivalent cation of mixed chemical character before exposure to the surfaces of the first and second components. Such organic multivalent cations may include ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), polyethyleneimine, chlorhexidine, or a polyamino acid. In certain embodiments, the organic multivalent cation of mixed chemical character is ethacridine, polyethylenimine or chlorhexidine or a salt thereof. In certain embodiments, the organic multivalent cation of mixed chemical character is ethacridine or a salt thereof. In certain such embodiments, the organic multivalent cation of mixed chemical character is present in an amount between approximately 0.01% and approximately 0.05%. In certain embodiments, the organic multivalent cation of mixed chemical character is present in an amount less than approximately 0.01%. In certain embodiments, the organic multivalent cation of mixed chemical character is present in an amount less than approximately 0.005%. In certain embodiments, the organic multivalent cation of mixed chemical character is present in an amount less than approximately 0.001%. In certain embodiments, the organic multivalent cation of mixed chemical character is present in an amount between approximately 0.020 and approximately 0.025%.

In certain embodiments, the sample is treated with one or more organic multivalent cations such as polyethyleneimine, polyallyamine, ethacridine, or chlorhexidine and salts thereof prior to the step of contacting the sample with the first and second components. In certain such embodiments, the organic multivalent cations used to treat the sample prior to the step of contacting the sample with the first and second components are provided in a concentration of less than 1%. In certain embodiments, the organic multivalent cations used to treat the sample prior to the step of contacting the sample with the first and second components are provided in a concentration between approximately 0.01% and approximately 0.05%, or in a concentration less than approximately 0.01%, or in a concentration less than approximately 0.005%, or in a concentration less than approximately 0.001%, or in a concentration between approximately 0.020 and approximately 0.025%.

In certain embodiments, the sample is additionally contacted with a soluble organic modulator selected from the group consisting of nonionic organic polymers, organic solvents, surfactants, and ureides, where such step of contacting the sample with soluble organic modulators occurs prior to the step of contacting the sample with the first and second components.

In certain embodiments, the sample is additionally contacted with an antiviral agent, where such step of contacting the sample with an antiviral agent occurs prior to the step of contacting the sample with the first and second components. In certain such embodiments, the antiviral agent is a non-multivalent organic cation such as benzalkonium chloride, methylene blue or tri (n-butyl) phosphate. In certain such embodiments, the antiviral agent is present in an amount less than approximately 1% (w/v), or in an amount less than approximately 0.1% (w/v), or in an amount less than approximately 0.01% (w/v), or in an amount less than approximately 0.001% (w/v).

In certain embodiments, the invention provides the additional steps of contacting the sample with a ureide in an amount sufficient for the ureide to be supersaturated in the protein preparation, and separating the supernatant containing the desired protein from the portion of the protein preparation, where such step of contacting the sample with such ureide occurs prior to the step of contacting the sample with the first and second components. In certain such embodiments, the ureide is urea, uric acid, hydantoin, allantoin, alcloxa, aldioxa, hemocane, ureidohydantoin, 5-ureidohydantoin, glyoxylureide, glyoxylic acid diureide, 2,5-dioxo-4-imidazolidinyl urea, or a purine. In certain such embodiments, the ureide is allantoin. In others, the ureide is uric acid. In certain embodiments, the allantoin is present in an amount greater than 0.5% (w/v), or in an amount greater than approximately 1% (w/v). In certain embodiments, the uric acid is present in an amount greater than 0.0025% (w/v), or in an amount greater than approximately 0.01% (w/v), or in an amount greater than approximately 0.1% (w/v), or in an amount greater than approximately 1% (w/v).

In certain embodiments, the organic modulator is a nonionic organic polymer selected from the group consisting of polyethylene glycol, polypropylene glycol and polybutylene glycol. In certain embodiments, the nonionic organic polymer has an average molecular weight of approximately 500 D or less. In certain embodiments, the organic modulator is an organic solvent such as ethylene glycol, propylene glycol, butylene glycol, dimethylsulfoxide, ethanol, or phenoxyethanol. In certain embodiments, the organic modulator is provided at a concentration of approximately 1% (w/v) or greater. In certain embodiments, the organic modulator is a surfactant selected from the group consisting of Tween, triton, CHAPS, CHAPSO and octyl glucoside. In certain such embodiments, the surfactant is provided at a concentration of approximately 1% (w/v) or less, or at a concentration of approximately 0.1% (w/v) or less. In certain embodiments, the organic modulator is a ureide provided in a subsaturating amount. In certain such embodiments, the ureide is selected from the group consisting of urea, hydantoin, and allantoin.

In certain embodiments, the invention provides a kit for the convenient practice of a method of the invention including some or all of the materials needed for performance of the invention, preferably in amounts and concentrations convenient for the performance of a method of the invention.

Terms are defined so that the invention may be understood more readily. Additional definitions are set forth throughout the detailed description.

"Aggregate(s)" refers to an association of two or more molecules that is stable at physiological conditions and may remain stable over a wide range of pH and conductivity conditions. Aggregates frequently comprise at least one biomolecule such as a protein, nucleic acid, or lipid and another molecule or metal ion. The association may occur through any type or any combination of chemical interactions. Aggregates of antibodies can be classified into two categories: "Homoaggregates" refers to a stable association of two or more antibody molecules; "Hetero-aggregates" refers to a stable association of one or more antibody molecules with one or more non-antibody molecules. The non-antibody component may consist of one more entities from the group consisting of a nucleotide, an endotoxin, a metal ion, a protein, a lipid, or a cell culture media component.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')$_2$, Fv, scFv, Fd, dAb, Fc and other compositions, whether or not they retain antigen-binding function.

"Electropositive surface" refers to a surface of a substrate or solid material which is dominated by positive charge. Electropositivity of a surface may be conferred by chemical groups including but not limited to weak anion exchange groups, like amino, ethylene diamino, diethylaminoethyl, polyallylamine, polyethyleneimine, strong anion exchange groups, such as quaternary amino groups, combined weak-strong exchangers, such as polylysine, polyarginine, or Tris(2-aminoethyl)amine, diethylenetriamine, triethylenetramine, tetraethylenepentamine, polypropylenimine tetraamine, PAMAM dendrimer (ethylenediamine core), deferoxamine or any combinations of the foregoing. Secondary functionalities that create a mixed chemical character on a positively charged surface may consist of negatively or positively charged groups, hydrophobic groups, pi-pi bonding groups, hydrogen-bonding groups, or metal-chelation groups. The secondary functionalities may exist on electropositive surfaces as an inadvertent byproduct of the manufacturing materials or process by which the particles are synthesized, or they may be present by deliberate design. The concentration of secondary functionalities may range from less than 1 milliequivalent per mL of particles, to more than 100 milliequivalents per mL.

"Electronegative surface" refers to a surface of a substrate or solid material which is dominated by negative charge. Electronegativity of a surface may be conferred by chemical groups including but not limited to so called weak cation exchangers, such as carboxyl, aminocarboxyl (iminodiacetic or nitriloacetic), or phosphoryl or strong exchangers such as sulfo, or sulfate moieties, $SO_3^-$. Secondary functionalities that create a mixed chemical character on a negatively charged surface may consist of negatively or positively charged groups, hydrophobic groups, pi-pi bonding groups, hydrogen-bonding groups, or metal-chelation groups. The secondary functionalities may exist on electronegative surfaces as an inadvertent byproduct of the manufacturing process by which the particles are synthesized, or they may be present by deliberate design. The concentration of secondary functionalities may range from less than 1 milliequivalent per mL of particles, to more than 100 milliequivalents per mL.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Metal affinity functionality" refers to the capacity of a chemical moiety, which may be immobilized on a surface, to bind metal ions preferably in a 1:1 fashion. Such moieties may have the capacity to form coordination bonds with a metal ion and certain such moieties may be bidentate or multidentate in character. Nonlimiting examples of electronegative moieties with this capability include iminodiacetic acid (2-(carboxymethylamino) acetic acid) and nitriloacetic acid (2,2',2"-Nitrilotriacetic acid). An example of an electropositive compound with this capability includes but is not limited to Tris(2-aminoethyl)amine or diethylenetriamine, triethylenetetramine, tetraethylenepentamine, polypropylenimine tetraamine, and deferoxamine.

"Non-ionic organic polymer" refers to a naturally occurring or synthetic hydrocarbon composed of linked repeating organic subunits that lack charged groups. It may be linear, dominantly linear with some branching, or dominantly branched. Examples suitable to practice the invention include but are not limited to polyethylene glycol (PEG), polypropylene glycol, and polyvinylpyrrolidone (PVP). PEG has a structural formula HO—(CH$_2$—CH$_2$—O)$_n$—H. Examples include, but are not limited to compositions with an average polymer molecular weight ranging from less than 100 to more than 1000 daltons.

"Organic multivalent cation" refers to an organic molecule, cation or salt of natural or synthetic origin that embodies at least one positive charge and at least one additional chemical functionality, thus rendering it multivalent. In certain embodiments, an organic multivalent cation the at least one additional chemical functionality is an additional positive charge such that the organic multivalent cation bears two or more positive charges bears. The organic multivalent cation (or OMC) may also bear negative charges such that it has a net positive or net neutral charge. Where the OMC is net positive it may be provided together with anions such as chlorides, bromides, sulfates, organic acids, lactates, gluconates, and any other anion not incompatible with the method. In certain embodiments certain of the positive charges of the OMC are supplied by amine, imine or other nitrogen moieties. The OMC may additionally be of mixed chemical character and include hydrophobic residues, other functional moieties and/or it may possess the ability to participate in other types of chemical interactions including, for example, the ability to participate in hydrogen bonds, hydrophobic interactions, pi-pi bonding, metal coordination, and intercalation. Examples of OMC in certain embodiments include but are not limited to the diamino acids, di-, tri, or larger homo- or hetero-peptides, such as polylysine, polyarginine, polyhistidine, polyornithine; polyethyleneimine; polyallylamine; polydimethrine, polymethylacrylamidopropyltrimethylarnmonia; polydiallyldimethylammonia; polyvinylbenzyltrimethylammonia; polyvinylguanidine; poly(N-ethyl-4-vinylpyridine; DEAE-dextran; DEAE-cellulose; ethacridine (CAS number 442-16-0; 7-ethoxyacridine-3,9-diamine); tris(2-aminoethyl) amine; guanidine; chlorhexidine; alexidine; citricidal, protamine; spermine; spermidine; salmine; chitosan; and variants and derivatives of the foregoing. For example, variants and derivatives of ethacridine are understood to include 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), and salts thereof (e.g. chlorides, bromides, sulfates, lactates, gluconates.)

"Organic solvent" refers to naturally occurring or synthetic organic compound existing in a liquid state. Examples suitable to practice the invention include but are not limited to ethylene glycol, propylene glycol, dimethyl sulfoxide, ethanol, and phenoxyethanol.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, pegylation, or conjugation with other chemical moieties. Examples of proteins include but are not limited to antibodies, clotting factors, enzymes, and peptide hormones.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Substrate" or "Solid material" refers to an insoluble organic solid that may be particulate, crystalline, polymeric, fibrous, porous-hollow fibrous, monolithic, membranaceous, in nature. It may consist of non-porous or porous particles, a porous membrane, a porous filter, or a porous monolith. If particulate, the particles may be roughly spherical or not, and may be of sizes ranging from less than 100 nm to more than 100 microns. The average pore size of porous particles may range less than 10 nm (microporous) to more than 100 nm (macroporous). The average pore size in membranes may range from less than 100 nm to more than 1 micron. The average channel size in membranes or monoliths may range from less than 1 micron to more than 10 microns. The solid material may further consist of compound constructions, for example in which particles are embedded in a reticular matrix, sandwiched between membranes, or both.

"Supersaturated ureide" refers to a solution containing an amount of ureide in excess of its maximum solubility under the conditions prevailing in a particular protein preparation. In certain embodiments, the invention provides a sample with a ureide present in an amount greater than such ureide's solubility in such sample under the conditions for such sample such that some fraction of such ureides is present in an undissolved form in the sample.

"Surfactant" includes "surface active agents" such as a class of organic molecules that generally embody a hydrophobic portion and a hydrophilic portion, causing them to be referred to as amphiphilic. At sufficient concentrations in aqueous solutions, surfactants can self-associate into clusters with the hydrophobic portions concentrated at the center to minimize contact with water, and the hydrophilic portions radiating outwards to maximize contract with water. In the presence of biological preparations, especially those containing materials that have a hydrophobic character or possess areas of hydrophobic character, the hydrophobic portion of surfactants tend to associate spontaneously with some portions of the hydrophobic material and increase their solubility through the influence of the hydrophilic portion of the surfactant. They may also be used to modulate hydrophobic interactions that occur between differing hydrophobic materials both dissolved in an aqueous solvent. Examples of surfactants suitable for practicing certain embodiments of the invention include but are not limited to nonionic surfactants such as polysorbate surfactants (e.g., Tween 20, Polyoxyethylene (20) sorbitan monolaurate, and Tween 80, Polyoxyethylene (20) sorbitan monooleate) and Triton (e.g., polyethylene glycol p-(1,1,3,3-tetramethylbutyl)-phenyl ether), and zwitterionic surfactants such as CHAPS (3-[(3-Cholamidopropyl)dimethylammonio]-1-propanesulfonate), CHAPS 0 (3-[(3-cholamidopropyl) dimethylammonio]-2-hydroxy-1-propanesulfonate), and octyl glucoside (e.g., (2R,3S,4S,5R,6R)-2-(hydroxymethyl)-6-octoxyoxane-3,4,5-triol).

"Ureide" refers to a cyclic or acyclic organic molecule of natural or synthetic origin that comprises one or more urea moieties or derivatives thereof. In certain embodiments, the invention provides ureides such as urea, uric acid, hydantoin, allantoin (CAS number 97-59-6; alcloxa, aldioxa, hemocane, ureidohydantoin, 5-ureidohydantoin, glyoxylureide, glyoxylic acid diureide, 2,5-dioxo-4-imidazolidinyl urea), purines, and derivatives thereof. In certain embodiments, the invention provides organic molecules of the formula R—CO—NH—CO—NH$_2$ or R—CO—NH—CO—NH—CO—R' or R' R"NH—CO—NR'"R"" where the relevant "R-groups" may be H or any organic moiety.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

The solid materials used to practice the invention may include insoluble particles of natural or synthetic origin, such as but not limited to porous microparticles commonly employed for practicing chromatography. Such particles may embody large pores that permit the diffusive entry of proteins, such as but not limited to antibodies; or they may embody small pores that allow the diffusive entry of small chemical species such as salts, sugars, and hetero-aggregate-dissociating agents, but are too small to permit the entry of proteins such as antibodies.

The solid materials may alternatively include non-porous particles, membranes or monoliths, fibers including porous-walled hollow fibers, porous membranes, and/or compound constructions employing combinations of the above elements.

The particles of mixed chemical character used to practice the certain embodiments of the invention particularly include insoluble organic particles. Such particles may be non-porous or porous. If porous, they may embody large pores that permit the diffusive entry of proteins, such as but not limited to antibodies; or they may embody small pores that allow the diffusive entry of small chemical species such as salts, sugars, and hetero-aggregate-dissociating agents, but are too small to permit the entry of proteins such as antibodies. The mixture of chemical characteristics embodied by such particles may include an electronegative functionality to scavenge soluble multivalent cation agents of mixed chemical character, and may further include one or more chemical functionalities that may enhance their ability to reduce aggregate content and/or facilitate the scavenging of soluble agents, including but not limited to electropositivity, hydrogen bonding, hydrophobic interactions, pi-pi bonding, and metal coordination.

Electropositive groups may include so-called strong anion exchange groups and/or so-called weak anion exchange groups. Electropositive groups of weak or mixed strong-weak anion exchange may be preferred for their ability to participate in coordination interactions with dissolved metal ions, producing the desirable result of removing contaminating metal ions from the applied biological sample. A non-limiting example of such a mixed weak-strong anion exchange group with metal coordination ability is Tris(2-aminoethyl)amine (TREN). Mixed chemical character may reside in a single complex chemical group, in separate chemical groups of distinct character on a single type of surface, on distinct surfaces, or any combination of the foregoing.

Electronegative groups may include so-called strong cation exchange groups or so-called weak cation exchange groups. Electronegative groups of weak or mixed strong-weak cation exchange may be preferred for their ability to participate in coordination interactions with dissolved metal ions, producing the desirable result of removing contaminating metal ions from the applied biological sample. Non-limiting examples of cation exchange groups with metal coordination ability include carboxy, phosphoryl, iminodiacetic (IDA), and nitriloacetic acid (NTA) groups. Weak ion exchange groups may also be preferred for their elevated ability to form hydrogen bonds in comparison to strong ion exchange groups. To the extent that the particles include one or more electropositive functionalities, they may be conferred by so-called strong anion exchange groups and/or so-called weak anion exchange groups.

In certain embodiments, the surfaces of the electropositive or electronegative materials may also embody hydrophobic groups of an aliphatic and/or or aromatic character, where the latter may be preferred because of their ability to participate in so-called pi-pi bonding. Mixed chemical character may reside in a single complex chemical group, in separate chemical groups of distinct character on a single type of surface, on distinct surfaces, or any combination of the foregoing.

In certain embodiments, one or more electronegative and/or one or more electropositive surface compositions may be employed simultaneously, and they may differ either with respect to their chemical composition and/or their physical form. Electropositive functionalities may be mediated by particles that are distinct and separate from electronegative particles. The particles may include porous or non-porous particles dispersed throughout the protein preparation, or packed in a column, or initially dispersed and then packed in a column.

Chemical functionalities of differing individual character may be employed in various ratios customized to the needs of a particular sample composition. For example, combinations intended for treatment of clarified cell culture supernatant may include an excess of electropositive surfaces, while combinations intended for treatment of supernatant already treated with electropositive hetero-aggregate-dissociating agents such as ethacridine or polyethyleneimine may include an excess of electronegative surfaces.

Soluble multivalent cations of mixed chemical character used to practice certain embodiments of the invention may include organic molecules with at least one positive charge and additional features that confer a mixed chemical character such as moieties providing the ability to participate in hydrogen bonding, hydrophobic interactions, pi-pi bonding, metal coordination, and intercalation. Examples of multivalent cations embodying these characteristics include polyethyleneimine, ethacridine, chlorhexidine, and numerous others. Such agents may be applied at concentrations ranging from 0.001% to 1.0% but will generally offer the best balance of aggregate reduction and protein product recovery when used at concentrations ranging from 0.01 to 0.10%, and particularly 0.02 to 0.06% or 0.02% to 0.05%.

In certain embodiments, the aggregate reducing performance of the method and/or the recovery of the desired protein may be enhanced by the co-addition of soluble organic agents that independently lack sufficient chemical influence to achieve the same level of aggregate reduction as other embodiments of the invention. Examples of such additional agents may include but are not limited to nonionic or zwitterionic surfactants such as Tween, Triton, Brij, CHAPS, CHAPSO, and octyl glucoside; organic polymers such as polyethylene glycol (PEG), polypropylene glycol, and polyvinyl pyrrolidone, preferably of a molecular weight less than 1000 Daltons; organic solvents such as ethylene glycol, propylene glycol, dimethyl sulfoxide, ethanol, propanol, isopropanol, phenoxyethanol; carbohydrates; and ureides including urea, hydantoin, and allantoin. Examples may also include soluble non-multivalent cation agents that are added for another purpose, such as but not limited to the inactivation of virus, including benzalkonium chloride, methylene blue, and tri(n-butyl)phosphate, among others. Examples in certain embodiments include ureides in supersaturating amounts, such as uric acid in amounts greater than 0.0025%, and allantoin in amounts greater than 0.56%.

Sequencing.

In certain embodiments, the multivalent cations and particles of mixed chemical character must be present together for a period sufficient to accomplish aggregate reduction. They may be added together, or the soluble agent added in advance for an indeterminate period. In some embodiments, advance addition of the multivalent cations may produce better results, but the other format will produce adequate results for many applications. The time required to practice the invention will depend directly on the concentration of the multivalent cations, the proportion of particles, and to a lesser extent the aggregate content of the protein preparation.

In certain embodiments, the invention provides method steps of preparing the sample for addition of the soluble and solid agents of mixed chemical character of the first and second components. The conditions should be of a nature to prevent substantial loss of the protein of interest through interactions with either the multivalent cations or particles. Such conditions will include a conductivity value sufficiently high to suspend strong charge interactions between the protein of interest and multivalent cations or the particles, and may include the inclusion of other additives to modulate other types of chemical interactions.

In certain embodiments, the invention provides effective aggregate reduction and removal of soluble agents at substantially elevated conductivity (salt concentration). Charged particles are particularly known for the dependency of their performance on aqueous environments of low conductivity, typically below 10 mS/cm, and most often below 5 mS/cm. These values equate roughly to 100 mM NaCl, and 50 mM NaCl, respectively. In certain embodiments, the invention supports effective aggregate reduction and removal of soluble agents at conductivity values of 20-30 mS, frequently up to 40 mS/cm, and sometimes up to 100 mS/cm, or more. Indeed, in certain embodiments, dissociation of hetero-aggregates increases at higher salt concentrations.

In certain embodiments, the invention provides the removal of sample components with the potential to foul chromatography columns used in subsequent purification methods. For example, IgG antibodies are very often purified by affinity chromatography with immobilized protein A. While effective, the chromatography media used to practice this method is extremely expensive and its useful cycle-life may be significantly reduced by application of crude samples. In certain embodiments, samples treated by the invention are sparklingly, optically clear and devoid of suspended debris that might impair the function of protein A or other chromatography media. In certain embodiments, purification of a sample according to a method of the invention will increase the IgG binding capacity of protein A by up to 10% or more, and offer a similarly beneficial effect on other capture or subsequent chromatography methods. In certain embodiments, use of the invention will permit protein A to reduce contaminating host protein content by a factor of 5 or more.

In certain embodiments, the invention provides methods which may enable subsequent purification methods that otherwise would be impaired by sample components even to the point of being impractical for initial antibody capture from unpurified sources. Host cell DNA, for example, binds more strongly to anion exchangers and hydroxyapatite media than IgG or IgM antibodies. This reduces both their antibody binding capacities and purification performance and impairs their suitability as initial capture methods. In certain embodiments, the invention promotes the removal of the majority of DNA before applying sample to these subsequent methods rendering both anion exchangers and hydroxyapatite media practical tools for initial antibody capture/purification.

In certain embodiments, in preparation for using the invention, it is advisable to evaluate the composition of the sample to be treated. The first major variable is the aggregate content of the sample. This can be determined easily using analysis by size exclusion chromatography, and particularly by monitoring the fractionation by simultaneous monitoring at wavelengths of 254-260 nm and 280 nm. This method is also convenient for detection of hetero-aggregates comprising antibody-DNA complexes, even when their hydrodynamic size closely approximates purified antibody. Samples that contain high aggregate levels, or contain aggregates that manifest a 254/280 ratio of 0.5 or greater, or contain antibody-DNA hetero-aggregates with elevated 254/280 ratios are favorable candidates for treatment of the sample with soluble agents of mixed chemical character, such as but not limited to ethacridine and/or polyethyleneimine, to promote dissociation of aggregates before exposing the sample to the surfaces of mixed chemical character. The term "high aggregate levels" is understood to be relative since it will depend on where in an overall purification process the sample derives from. "High" aggregate levels in cell culture supernatant may be up to 50% or more compared to the antibody, whereas "high" aggregate levels after initial purification might include anything over 5%, or even less.

In certain embodiments, it will also be advisable to evaluate the native chemical character of the protein to be purified. IgG antibodies tend to be of electro-neutral-to-alkaline in character with weak or no tendency to bind electropositive surfaces but mild-to-moderate tendency to bind electronegative surfaces. IgM antibodies range from alkaline to acidic in character, generally with a strong tendency to bind electropositive surfaces, and with mild to moderate tendency to bind electronegative surfaces. Practical determination of an antibody's surface character can be accomplished by a pair of simple experiments in which the antibody is applied to a cation exchanger at pH 7.0 and eluted with a linear salt gradient, and applied to and eluted from an anion exchanger under the same conditions. The salt concentration at which the antibody elutes from each exchanger provides a convenient index of the antibody's relative tendencies to bind electronegative or electropositive surfaces, and the salt concentrations required to control such interactions. Such characterization can be performed at multiple pH values to obtain a more complete understanding of the charge characteristics of a particular protein of interest.

In certain embodiments, it will be desirable to select one or more multivalent cations of mixed chemical character. Experimental data reveal that as a general matter, the less hydrophobic the multivalent cation, the higher the recovery of the protein of interest. Also, the less hydrophobic, the wider and higher the concentration range over which the multivalent cation can be applied without significant loss of protein. Thus weakly hydrophobic PEI may be considered a better candidate than the more hydrophobic ethacridine, or the much more hydrophobic chlorhexidine. However, other issues may also need to be taken into consideration in addition to product recovery. PEI embodies well-known cytotoxic properties, and it is difficult to detect with adequate sensitivity to easily validate its removal from a sample through the course of a purification process. Ethacridine may be preferred because of its long history in the field of plasma protein fractionation and as an antiviral agent. In addition, its bright yellow color and intrinsic fluorescence facilitate sensitive measurement of its content in a given sample, thereby aiding documentation of its removal subsequent to practicing the method. Besides that, different multivalent cations may embody different secondary chemical functionalities that bear on their ability to mediate the desired effect. PEI for example is understood to bind DNA chiefly through electrostatic interactions and hydrogen bonding. Ethacridine offers fewer opportunities for both interactions but is known to intercalate DNA. It also generally supports more effective aggregate reduction.

In certain embodiments, agents such as ethacridine, chlorhexidine, and polyethyleneimine may be effectively applied at concentrations ranging from less than 0.001% to 1%, depending on the characteristics of the antibody and the composition of the sample. The lowest effective concentrations will be preferred in most cases because high concentrations may increase the amount of electronegative solids of mixed chemical character required to remove the soluble agents. Experimental data reveal concentrations of 0.01 to 0.1 to fulfill this ideal, and particularly concentrations ranging from 0.02 to 0.06% or 0.02% to 0.05%. The most effective agent and working concentration can be identified and customized for each specific case. It will be apparent to the person of ordinary skill that certain of the above-mentioned agents are known for their ability to inactivate virus, and will have the additional benefit of augmenting the removal of DNA and endotoxins. More than one species of multivalent cation may be employed. Pre-treatment of the sample with multivalent cations may increase the ability of the invention to achieve low aggregate levels in some embodiments.

In certain embodiments, it may be advisable to evaluate electropositive and/or electronegative substrates of various character to best accommodate the characteristics of the desired protein and the feed stream in which it resides. For example, in some cases an electropositive material having quaternary amine functional groups may have lesser ability to reduce aggregates and/or other contaminants, but support higher recovery of the desired protein, while an electropositive material in the form of TREN may support the opposite results. In some cases an electropositive surface that is preferred for one desired protein, may be judged inferior for another. For example, TREN may be preferred for IgG; while quaternary amine may be preferred for IgM. The density of the ligands on a substrate may also influence the performance of certain embodiments of the invention such as through secondary interactions between sample component and the chemical surface(s). For example, experimental data document that in certain embodiments, substrates having a high density of TREN may outperform substrates having a low-density of TREN In certain embodiments, it may be convenient to begin with an equally balanced mixture of particles of mixed chemical character, at a combined volumetric ratio of 5% solids to sample. Through the course of optimizing the system to best accommodate the needs of a particular sample, the ratio of solids to sample volume may be reduced to identify the effectivity threshold for that particular sample/treatment system. The ratio of electronegative to electropositive functionalities may also be varied, as may be the choice of secondary chemical functionalities included on the surface(s). The experimental workload to evaluate these variations can be substantially reduced by applying statistically based Design of Experiments (so-called DoE). Convenient particles of mixed chemical character may include commercial anion exchangers and cation exchangers, chelating resins, hydrophobic resins, and products marketed to perform so-called mixed-mode chromatography.

In certain embodiments, initial conditions for evaluation should be performed at pH and conductivity values that prevent antibody loss through binding to the various surfaces, but beyond that, experiments should specifically evaluate higher conductivity levels since they may support enhanced dissociation of aggregates and/or antibody-contaminant complexes. As a matter of convenience, initial experiments with IgG antibodies can be conducted at a pH of 6.5-7.5 and a conductivity of 10-15 mS/cm. Initial experiments with IgM antibodies can be conducted at the same pH but a conductivity of 20-30 mS/cm. Subsequent experiments with each can be performed with higher and lower conductivities, and/or higher or lower pH values to identify the conditions that support the best combination of aggregate reduction and antibody recovery. Although it is not a primary object of the invention to reduce levels of host cell protein contaminants, it may offer a significant contribution in this regard, in particular with respect to the content of highly alkaline and/or highly acidic host proteins.

In certain embodiments, the period of time which the soluble and solid agents of mixed chemical character should be present can be determined by simple experiments, in which samples are analyzed by SEC over a time course, for example every 10 minutes for 1 hour, or other increments and durations as indicated by data from the examples as described below.

It will be apparent to the person of ordinary skill in the art that, in addition to reducing the content of homoaggregates and hetero-aggregates, certain embodiments of the invention may also substantially reduce the content of host cell protein, DNA, endotoxin, and virus.

In certain embodiments, the solid materials of the first and second components may be cleaned and recycled after use. In other embodiments, they may be discarded after use. In certain embodiments, a method of the invention may be practiced prior to other chromatography steps, where this practice has the dual benefit of protecting the chromatography media from fouling by cell culture media components, and improving the quality of purification by virtue of having put the target product in a more homogeneous state than it was in the untreated sample.

In certain embodiments, the invention may provide methods for the use of electronegative particles and electropositive particles mixed and enclosed by neutral materials, embedded in neutral materials, or enclosed by or embedded in materials that are themselves electronegative and/or electropositive. In certain embodiments, the electronegative and/or electropositive surface may comprise additional chemical functionalities, including but not limited to the ability to participate in hydrophobic interactions, pi-pi bonding, hydrogen bonding, and metal affinity.

Additional objects and advantages of the invention will be set forth in part in the description which follows, and in part will be obvious from the description, or may be learned by practice of the invention. The objects and advantages of the invention will be realized and attained by means of the elements and combinations specified in the claims.

It is to be understood that both the foregoing general description and the following detailed description are exemplary and explanatory only and are not restrictive of the invention, as claimed.

EXAMPLES

The following examples illustrate prototypes demonstrating the efficacy of certain embodiments of the invention.

Example 1

Dissociation of DNA-antibody hetero-aggregates with integrated removal of DNA by treatment with a prototype mixture of electropositive and electronegative surfaces. Sodium chloride (NaCl) to a final concentration of 200 mM was added to 100 mL clarified cell culture supernatant containing monoclonal IgM clone 85 (conductivity 21 mS/cm). 2.5 mL of an electropositive macroporous particulate material (Nuvia Q) was mixed with 2.5 mL of an electronegative macroporous particulate material (Nuvia S), then sandwiched between polyvinylidene difluoride (PVDF) filters. The particles were equilibrated with 50 mM Hepes, 200 mM NaCl, pH 7.0. The sample was flowed through the particles, then chased with equilibration buffer. The particles were cleaned with 3 M guanidine. Untreated and treated sample were applied to an analytical size exclusion chromatography (SEC) column, monitored at 254 and 280 nm UV. The 254/280 ratio of the IgM peak in the untreated sample was 0.546, indicating that a substantial amount of DNA was associated with the IgM. The 254/280 ratio of the IgM peak following treatment was 0.449, indicating far lower DNA content. Aggregate content was reduced from about 3% to less than 1%. This experiment, and the following experiments describing results with IgM monoclonal antibodies were performed using cell cultures that were grown to 80-100% mortality, which will be understood by persons experienced in the art to represent worst-case scenarios in terms of the content of aggregates and contaminants in the sample. It will thus be apparent that cell cultures harvested at higher levels of cell viability, as is common in most commercial applications, may be accommodated with substantially lower volumes and likely different compositions of mixed chemistries. In a parallel experiment with a different IgM clone (IgM-529), it was necessary to elevate conductivity to 25 mS/cm to avoid antibody losses on the particles.

Example 2

Hetero-aggregate dissociation and removal of contaminants from an IgM preparation at elevated NaCl concentration. 100 mL of cell culture supernatant containing IgM 85 and with salt added to achieve a conductivity of about 25 mS/cm was passed over a prototype mixture of 0.25 mL each of a macroporous electronegative solid phase (Nuvia S), a macroporous electropositive solid phase (Nuvia Q), a microporous electropositive solid phase (Q Sephadex A25), and a microporous electronegative solid phase (CM-Sephadex C25), sandwiched between PVDF filters, and equilibrated with 50 mM Hepes, 250 mM NaCl, pH 7.0. Fractions were collected to determine efficacy. HMW aggregates and hetero-aggregates were essentially absent at sample loads up to about 20 mixed-particle volumes. More than 90% of the DNA was removed even at sample loads up to 100 particle volumes. These results demonstrate effective use of the invention at a conductivity value more than 30% higher than the minimum required to avoid loss of IgM. IgM recovery was 98%.

Example 3

Hetero-aggregate dissociation and removal of contaminants from an IgG preparation at elevated NaCl concentration. A monoclonal IgG, clone Her2, was found not to bind to electropositive media (Nuvia Q) even at conductivities below 1 mS/cm. It was found not to bind to electronegative media (Nuvia S) at conductivities above 12 mS (pH 7.0). The sample was raised to a conductivity of 15 mS and passed over the same prototype mixture as described in Example 2. DNA was removed, along with about half of the host protein contaminants. HMW aggregates were reduced from greater than 10% to less than 0.2%. Hetero-aggregates, as determined by 254/280 ratio, were essentially eliminated. This and the following experiments describing results with IgG monoclonal antibodies were performed using cell cultures that were grown to 50-80% mortality, which will be understood by persons experienced in the art to represent worst-case scenarios in terms of the content of aggregates and contaminants in the sample. It will thus be apparent that cell cultures harvested at higher levels of cell viability, as is common in most commercial applications, may be accommodated with substantially lower volumes and likely different compositions of mixed chemistries.

Example 4

10 mL of the same mixture of solid materials described in Example 2 was sandwiched between woven nylon retainers (porosity about 5 μm) in a cylindrical glass assembly. The particles were equilibrated with 50 mM Hepes, 150 mM NaCl, pH 7.0. 500 mL of cell culture supernatant containing a monoclonal IgG was flowed through the particles and collected. The sample was chased with equilibration buffer to enable collection of the processed sample. The flow-through contained monoclonal IgG with HMW aggregate content less than 0.2% and no apparent hetero-aggregates. The particles were eluted with 50 mM Hepes, 2 M NaCl, yielding an intensely colored yellow-brown eluate.

Example 5

100 mg of ethacridine was added stifling to 1 L of cell culture media containing an IgG monoclonal antibody and incubated for 15 minutes before removing a yellow precipitate by centrifugation. 80 mL of the same mixture of solid materials described in Example 2 was sandwiched between woven nylon retainers in a glass assembly. The yellow-tan colored but optically clear supernatant from the ethacridine treatment was flowed over the particles and collected. The sample was chased with equilibration buffer to enable collection of the processed sample. The column was eluted with a step to 50 mM Hepes, 2 M NaCl, pH 7.0. The salt elution peak was roughly half the size obtained with untreated sample due to elimination of DNA by the ethacridine treatment. The ratio of UV absorbance at 280 and 254 nm was calculated for each sample. The untreated sample gave a 280/254 ratio of 2.06. The ethacridine treated sample gave a ratio of 2.33, indicating substantially reduced hetero-aggregate content. The flow-through sample gave a ratio of 2.39, indicating removal of yet another increment of DNA. HMW aggregates were reduced to less than 0.1%. A previous experiments with a mixed-media volume equivalent to 2% of the applied sample volume was inadequate to fully remove ethacridine. Parallel experiments showed that a bed height of at least 5 cm gave the best results with the smallest volume of mixed-media.

Example 6

A prototype particle mixture was prepared from 0.5 mL of chelating porous particles (Chelex-100) and 0.5 mL electropositive porous particles (Macroprep High-Q), mixed and sandwiched between cellulose filters in a glass assembly. A purified sample of IgG monoclonal antibody (Her2) was passed over the particles without loss at near-physiological conditions: pH 7.0, 10 mS/cm. Experiments with unpurified antibody were conducted at 25 mS/cm, 20 mS/cm, and 30 mS/cm. Hetero-aggregates and HMW aggregates were removed in all cases. Experiments with unpurified antibody containing 0.02% ethacridine were conducted at the same conductivities. Hetero-aggregates and HMW aggregates were removed in all cases, and the flow-through was free of ethacridine as documented by the lack of UV absorbance at 365 nm.

Example 7

In a set of experiments parallel with Example 6, a purified sample of IgM monoclonal antibody (clone 529) was passed over the particles without loss at elevated salt conditions: pH 7.0, 200 mS/cm. Unpurified antibody, and unpurified antibody containing 0.02% ethacridine were applied at 20, 30, and 40 mS/cm. Hetero-aggregates and HMW aggregates were removed in all cases, and the flow-through was free of ethacridine as documented by the lack of UV absorbance at 365 nm. These experiments were repeated with 0.2% ethacridine. Hetero-aggregates and HMW aggregates were removed in all cases, and the flow-through was free of ethacridine.

Example 8

Capacity study of the removal of DNA and aggregates from a monoclonal IgM culture supernatant when passed over a packed bed consisting of an equivolume mixture of Chelex-100 and MacroPrep High Q. A 0.5 mL each of Chelex-100 and MacroPrep High Q were sandwiched between PVDF membranes. M529 culture supernatant was loaded at 1 mL/min and samples of the flow-through taken at 25, 50. And 100 mL were analyzed by analytical SEC. Even at maximal loading, 254-dominant hetero-aggregates were essentially eliminated from the flow-through. IgM recovery at the various loads (low to-high) was 58, 73 and 85% respectively. The experiment was repeated with NaCl added to produce a conductivity of 25 mS/cm. Heteroaggregate reduction was unaffected but recovery increased to about 85, 90, and 95% respectively.

Example 9

The experiment of Example 8 was repeated but with a combination of microporous and macroporous electropositive and electronegative media, plus microporous lipophilic particles in equal volumes: QAE Sephadex A-25, SP Sephadex C-25, Nuvia Q, Nuvia S and Sephadex LH-20. Allantoin and ethacridine were added to 5% serum-supplemented monoclonal IgM supernatant, to final concentrations of 1% (super-saturation) and 0.02% respectively. The supernatant was clarified by centrifugation and then flowed through the bed (20 mL supernatant per mL packed bed). The IgM was then captured over a cation exchanger. IgM recovery was 80% over the two-step process and the purity was more than 90% by analytical SEC, with no apparent aggregates.

Example 10

0.6 mL each of electronegative, metal coordinating porous particles (Chelex-100) and electropositive porous particles (Macroprep High Q) were added to 45 mL of M529 IgM clarified culture supernatant immediately following addition of ethacridine to a final concentration of 0.02%, at a conductivity of 25 mS/cm, and mixed continuously on a rotary shaker. Samples were drawn at 10 minute intervals for an hour. Analytical SEC showed progressive reduction of HMW and hetero-aggregates, nearly reaching completion at 50 minutes, but improving slightly with an additional 10 minutes. Ethacridine was also removed as indicated by the profiles at 365 nm.

Example 11

One liter of monoclonal IgG-containing cell culture supernatant was treated with 1% allantoin and 0.02% ethacridine for 15 minutes. The yellow precipitate was removed by membrane filtration, and the optically sparkling clear bright yellow filtrate was applied to 10 mL column filled with an equal mixture of Chelex 100 and Macroprep High Q. The treated material was then applied to a protein A column to a load of 20 mg/mL, washed for 10 column volumes, and the IgG eluted. Comparison of the eluted IgG with antibody eluted from protein A loaded with untreated cell culture supernatant contained roughly 5 times lower host cell protein contaminants. Parallel experiments were set up to determine the dynamic binding capacity of protein A columns loaded with treated and non-treated samples. Dynamic capacity on the column loaded with treated sample was about 10% higher than the column loaded with untreated sample.

Example 12

An equal mixture of microporous styrenedivinylbenzene particles bearing iminodiacetic acid groups (Chelex 100) and macroporous agarose particles bearing tris(2-aminoethyl)amine (BioWorks TREN, hi-sub) was sandwiched between polyethylene frits and equilibrated with 50 mM Hepes, 100 mM NaCl, pH 7.0. Filtered mammalian cell culture supernatant containing IgG (Clone HER2) was passed through the assembly and analyzed by size exclusion chromatography. The untreated sample contained about 10% aggregates. The treated sample contained less than 0.2% aggregates. Testing with AccuBlue revealed that treatment also removed about 95% of the DNA.

Example 13

The particle mixture of example 12 was equilibrated to 50 mM Hepes, 100 mM NaCl, pH 7.0 and added directly to the filtered mammalian cell culture supernatant containing IgG (Clone HER2), incubated stifling for 1 hour, then removed by membrane filtration. Analysis revealed roughly half the aggregate reduction and DNA removal of example 12. Incubation stirring for 16 hours at 4 exhibited about 80% the efficiency of example 12.

Example 14

An equal mixture of negatively charged metal-chelating styrene divinylbenzene particles (Chelex 100), positively charged polymethacrylate porous particles (Macroprep Hi-Q), and negatively charged polymethacrylate particles (Macropre Hi-S) was mixed with a sample of IgM-529 that had been previously treated with NaCl to a final conductivity of 20 mS/cm, 1% allantoin, and 0.025% ethacridine. The volumetric ratio of particles to sample was 1:20. Samples were taken at 10 minutes, 20 minutes, 40 minutes, and 60 minutes, and the particles were removed by microfiltration. FIG. 1 shows a dramatic reduction of high molecular weight aggregates at all time points, but with progressively greater reduction of all aggregates over time, accompanied by a substantial apparent reduction of host cell protein contaminants as well. Subsequent analysis showed that the reduction of both aggregates and host proteins reflected the combined reduction of chromatin remnants from the sample. Ethacridine was also removed from the samples at all time points.

Example 15

Figure 2A:
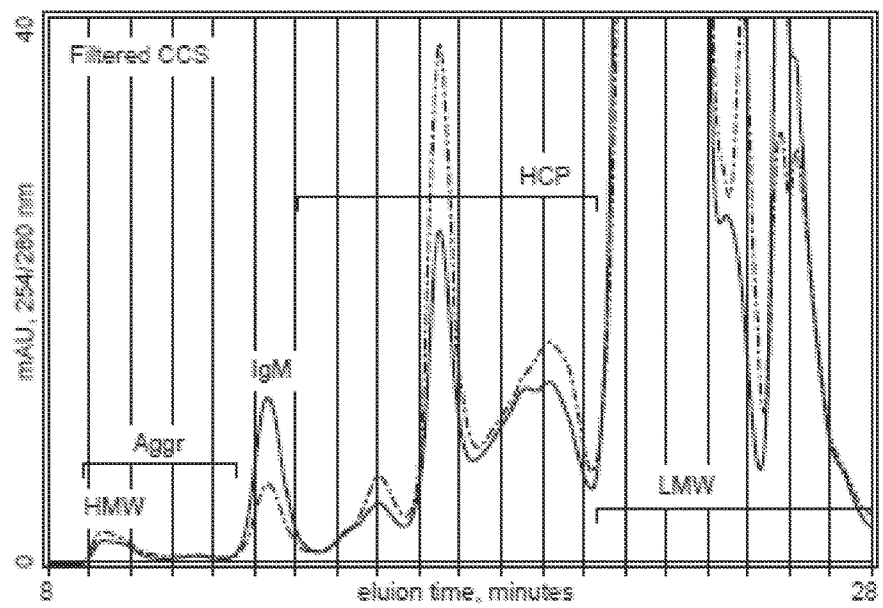
FIG. 2A shows an SEC profile of IgM-84 filtered cell culture supernatant (CCS). Aggr: aggregates. HMW: high molecular weight aggregates. HCP: host cell protein. LMW: low molecular weight cell culture media components. Solid line: 280 nm. Broken line: 254 nm.
Figure 2B:
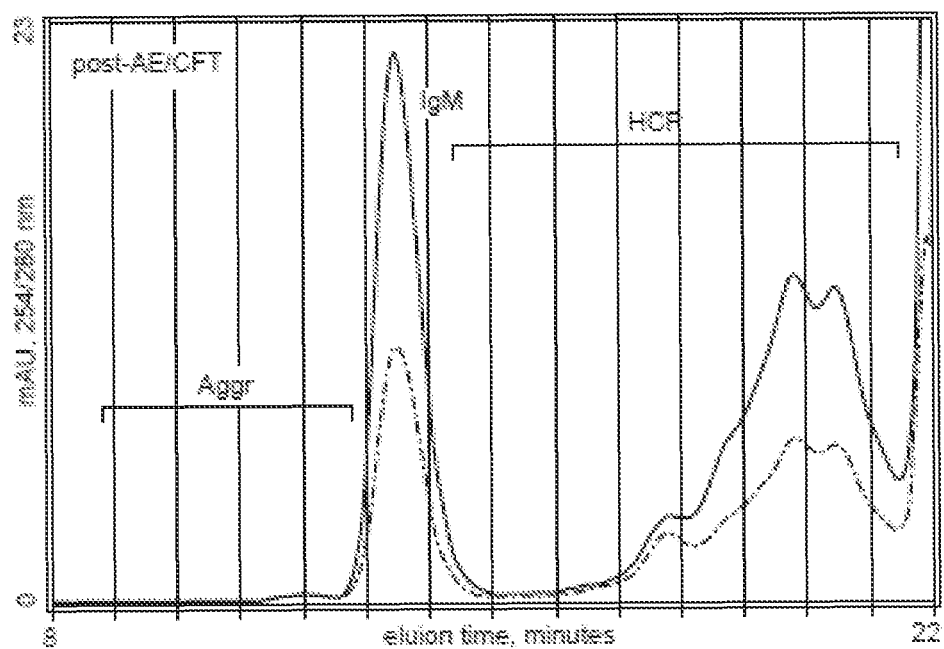
FIG. 2B shows an SEC profile of the IgM-84 filtered CCS of FIG. 2A after allantoin-ethacridine and column flow through treatment. Aggr: aggregate. HCP: host cell protein. Solid line: 280 nm. Broken line: 254 nm.

FIGS. 2A and 2B illustrate size exclusion chromatography profiles before and after treatment of IgM-84 treated with NaCl, allantoin, and ethacridine as in Example 7, and then treated with the same media mixture as in Example 7, but by passing the sample though a device in which the mixed media were sandwiched between woven polymer retainers of adequately narrow mesh to retain the particles. HMW aggregate was completely eliminated, along with the majority of smaller aggregates. Table 1 below shows that DNA and histones were initially distributed across all aggregate fractions, with the IgG fraction, and across all protein-containing fractions.

TABLE 1

IgM and contaminant content of SEC fractions.

| EIT, min | [IgM] | DNA size | [DNA] | [His] | 254:280 |
|---|---|---|---|---|---|
| 9 | 0.31 | bld | 10 | 0.13 | 1.31 |
| 10 | 0.09 | bld | 10 | 0.11 | 1.30 |
| 11 | 0.42 | bld | 10 | 0.13 | 1.03 |
| 12 | 0.68 | (150-1000) | 12 | 0.13 | 0.98 |
| 13 | 20.29 | bld | 44 | 0.21 | 0.49 |
| 14 | 21.08 | (660) | 236 | 0.76 | 0.89 |
| 15 | 2.33 | 445/(660) | 459 | 1.87 | 0.97 |
| 16 | 0.30 | 316/445 | 435 | 0.82 | 1.59 |
| 17 | 0.51 | 316 | 796 | 1.09 | 1.45 |
| 18 | 0.38 | 155/316 | 314 | 0.96 | 1.60 |
| 19 | 0.31 | 90/155 | 339 | 0.33 | 1.40 |
| 20 | 0.09 | 90 | 684 | 0.86 | 1.56 |
| 21 | bld | 58 | 123 | 1.33 | 0.90 |
| 22 | bld | bld | 23 | 0.54 | 1.21 |
| 23 | bld | bld | 13 | bld | 3.67 |
| 24 | bld | bld | 3 | bld | 15.86 |

EIT: elution time, minutes.
[IgM]: concentration in micrograms/mL.
DNA size in base pairs (bp). Values in parentheses from DNA detected in ion exchange experiments.
[DNA] concentration in ng/mL.
[His]: total histone concentration, micrograms/mL.
bld: below limit of detection.

Example 16

Table 1 also illustrates the size distribution of DNA, which led to the unexpected discovery that some aggregate populations included nucleosomal arrays containing various numbers of nucleosomes, in addition to DNA and histones. Recovery of IgM from this treatment was 98%.

Example 17

Figure 3:
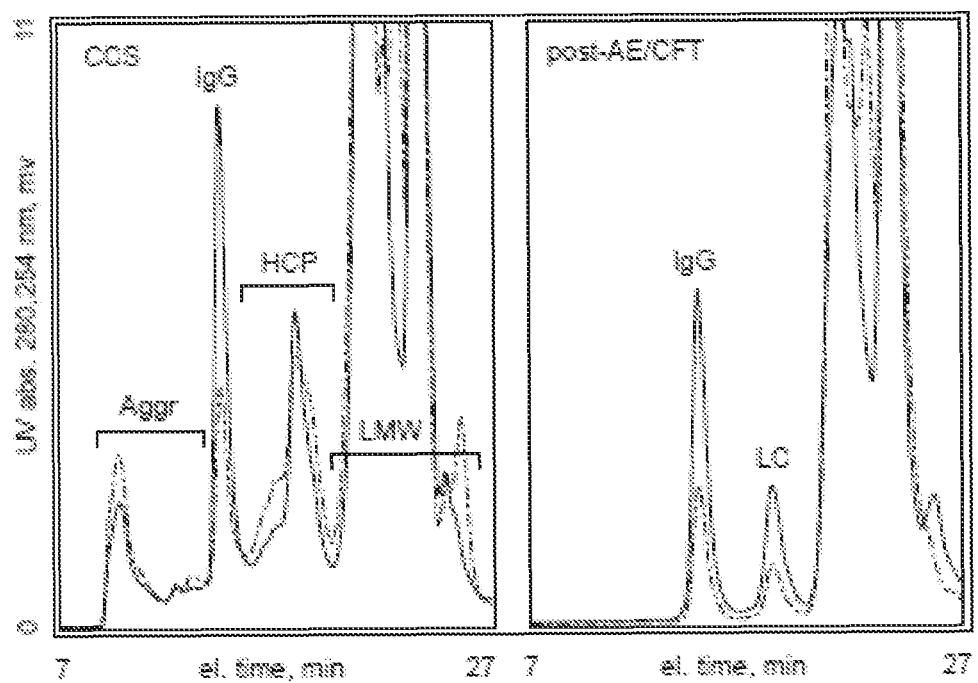
FIG. 3 shows an SEC profile of monoclonal IgG HER2 CCS before (left panel) and after (right panel) treatment with allantoin-ethacridine and column flow through treatment. Aggr: aggregate. HCP: host cell protein. LMW: low molecular weight cell culture media components. LC: light chain. Solid line: 280 nm. Broken line: 254 nm.

FIG. 3 illustrates size exclusion chromatography profiles before and after the same procedure of Example 16 of an anti-HER2 monoclonal IgG antibody. The results are the same in kind, but improved in degree over Example 8, likely, at least in part, because the concentration of the antibody in the original cell culture supernatant is about 10 times higher.

Example 18

1 L of cell culture harvest was treated by addition of 1% allantoin and 0.025% ethacridine and incubated stifling for 15 minutes, after which the cells and other particulates were removed by centrifugation. The supernatant was passed through an assembly containing equal proportions of styrene divinylbenzene particles substituted with iminodiacetic acid (Chelex 100), agarose particles substituted with TREN (BioWorks TREN, hi-sub), and acrylate particles substituted with butyl residues (Macroprep T-butyl), with a combined volume of 50 mL, dimensions of 2.6×10 cm, and a flow rate of 25 mL/min. Initial aggregate content of greater than 12% was reduced to less than 0.1%. Excess ethacridine was removed. Host protein contamination was reduced 60%, from 240,000 ppm to 142,000 ppm. DNA, as measured by qPCR was reduced by 6 logs. Antibody recovery was 99%. Turbidity was 2.0 NTU (nephelometric turbidity units). Analytical SEC showed 2 extremely-late eluting components that were interpreted to represent extreme-hydrophobic cell culture media additives.

Example 19

1 L of cell culture harvest was treated by addition of 1% allantoin and 0.025% ethacridine and incubated stifling for 15 minutes, after which the cells and other particulates were removed by centrifugation. The supernatant was passed through an assembly containing equal proportions of styrene divinylbenzene particles substituted with iminodiacetic acid (Chelex 100), styrene divinylbenzene particles substituted with amino groups (Dowex AG1x8), and acrylate particles substituted with butyl residues (Macroprep T-butyl), with a combined volume of 50 mL, dimensions of 2.6×10 cm, and a flow rate of 25 mL/min. Initial aggregate content of greater than 12% was reduced to less than 0.1%. Antibody recovery was 95%. Results were otherwise identical to example 18.

Example 20

1 L of cell culture harvest was treated by addition of 1% allantoin and 0.025% ethacridine and incubated stifling for 15 minutes, after which the cells and other particulates were removed by centrifugation. The supernatant was passed through an assembly containing equal proportions of styrene divinylbenzene particles substituted with iminodiacetic acid (Chelex 100), styrene divinylbenzene particles substituted with amino groups (Dowex AG1x2), and agarose particles substituted with TREN (BioWorks TREN, hi-sub) with a combined volume of 50 mL, dimensions of 2.6×10 cm, and a flow rate of 25 mL/min. Initial aggregate content of greater than 12% was reduced to less than 0.1%. Antibody recovery was 95%. Analytical SEC indicated the absence of the extremely-late eluting components observed in Example 18. Results were otherwise identical to example 18.

Example 21

The experiment of example 20 was repeated except reducing the proportion of Dowex AG1x2 by half, and adding the same increment of T-butyl, thereby creating a 2:2:1:1 mix of Chelex, BioWorks TREN, Dowex, and T-butyl. Antibody recovery was 98%, and SEC indicated removal of the late-eluting components. This example, in combination with examples 18-20, highlights how the choice of surface chemistries and their proportions can be adjusted to accommodate a particular sample to target particular contaminants or classes of contaminants.

Example 22

1 L of an Fab fragment produced in *Escherichia. coli*, recovered by osmotic shock with sucrose, and then filtered to remove cell debris, was combined with 1% allantoin, 0.025% ethacridine, and incubated stifling for 15 minutes prior to be passed over 50 mL of an equal mixture of Macroprep Hi-S (electronegative) and Macroprep Hi-Q (electropositive) sandwiched between polyethylene frits. Conditions in the column were 20 mM sodium phosphate, 150 mM NaCl, pH 6.7. Sample conductivity and pH were adjusted to the same conditions. DNA was reduced by 99% as measured by AccuBlue. Host protein was reduced by about 65% as measure by ELISA. Fab recovery was 97% and the processed sample was optically clear.

It will be apparent to persons skilled in the art, given the wide diversity of cells, cell culture formulations, product characteristics and expression levels, and relative cell mortality at harvest, that to best accommodate any given protein produced in any given cell culture medium, and harvested within a particular range of cell mortalities will require that the specific types of particles, their relative volumes, and the specific conditions will need to be developed experimentally on an individual basis. It will be further apparent, based on the examples and guidelines provided here, that the experiments required to identify the best combination of materials and conditions is within the purview of a person of ordinary skill in the art.

After use, the solid charged materials may optionally be discarded or regenerated.

The present invention may be combined with various purification methods to achieve the desired levels of purification. Examples include, but are not limited to, other methods commonly used for purification of antibodies, such as protein A and other forms of affinity chromatography, anion exchange chromatography, cation exchange chromatography, hydrophobic interaction chromatography, immobilized metal affinity chromatography, and additional mixed mode chromatography methods. It is within the purview of a person of ordinary skill in the art to develop appropriate conditions for the various methods and integrate them with the invention herein to achieve the necessary purification of a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method of reducing the aggregate content of a sample containing an antibody or antibody fragment, wherein the method comprises the steps of: (i) contacting the sample with a ureide in an amount sufficient for the ureide to be supersaturated in the sample; (ii) separating a supernatant containing the antibody or antibody fragment from solid or undissolved portions of the sample; (iii) providing a first component which is a first solid substrate having an electronegative surface, wherein the electronegativity of the surface of the first component is conferred in part by a moiety selected from the group consisting of iminodiacetic acid, ethylene glycol(aminoethylether)diacetic acid, nitriloacetic acid, aspartic acid, glutamic acid, a carboxylic acid, sulfurous acid, sulfonate, and phosphoric acid; (iv) providing a second component which is a second solid substrate having an electropositive surface, wherein the electropositivity of the surface of the second component is conferred in part by a moiety selected from the group consisting of tris(2-aminoethyl)amine, diethylenetriamine, triethylenetetramine, tetraethylenepentamine, polypropylenimine tetramine, PAMAM dendrimer (ethylenediamine core), deferoxamine, a primary amino group, a secondary amino group, a tertiary amino group, and a quaternary amino group; (v) contacting the supernatant with the first and second components, wherein the first and second substrates are provided as a plurality of particles packed in a column, and the operating conditions substantially prevent the binding of the antibody or antibody fragment to the first or second components; and (iv) separating a resulting sample containing the antibody or antibody fragment with a reduced aggregate content from the first and second components.

2. The methods of claim 1, wherein the sample or supernatant is contacted with a soluble organic multivalent cation of mixed chemical character prior to contacting the supernatant with the first and second components.

3. The method of claim 2 wherein the sample or supernatant is incubated with the soluble organic multivalent cation of mixed chemical character for a period of time prior to contacting the first and second components.

4. The methods of claim 1, wherein the supernatant is incubated with the first and second components for a period of time.

5. The methods of claim 2, wherein the organic multivalent cation having mixed chemical character is removed from the sample in the step of separating the sample with a reduced aggregate content from the first and second components to the extent that the organic multivalent cation having mixed chemical character is associated with the substrate of the first or second component.

6. The method of claim 1, wherein the particles of the first substrate, the second substrate or both are non-porous.

7. The method of claim 1, wherein the particles of the first substrate, the second substrate or both are porous.

8. The method of claim 7 wherein the pore size of the porous particles is large enough to permit entry of a protein in a protein preparation.

9. The method of claim 7 wherein the pore size of the porous particles is too small to permit entry of a protein in a protein preparation.

10. The method of claim 7 wherein the average pore size of the porous particles is between about 10 nm and about 100 nm.

11. The methods of claim 1, wherein the particles are sandwiched between porous membranes or monoliths.

12. The methods of claim 1, wherein the particles are sandwiched between woven or amorphous fibrous filters.

13. The methods of claim 1, wherein the particles are sandwiched between crystalline frits.

14. The methods of claim 1, wherein the particles are embedded in a reticular polymer network.

15. The method of claim 2, wherein the conductivity of the sample is greater than 20 mS/cm.

16. The method of claim 15 wherein the conductivity of the sample is greater than 30 mS/cm.

17. The method of claim 15 wherein the conductivity of the sample is greater than about 40 mS/cm.

18. The method of claim 15 wherein the conductivity of the sample is greater than about 100 mS/cm.

19. The method of claim 1, wherein the aggregates comprise homo-aggregates of the antibody or antibody fragment.

20. The method of claim 19 wherein the presence of homo-aggregates of the antibody or antibody fragment is substantially eliminated.

21. The method of claim 1, wherein the aggregates comprise hetero-aggregates of the antibody or antibody fragment and a contaminant.

22. The method of claim 21 wherein the hetero-aggregates are of substantially the same hydrodynamic size as the antibody or antibody fragment.

23. The method of claim 21 wherein the contaminant is a nucleic acid, nucleotide, endotoxin, metal ion, protein, lipid, or cell culture media component.

24. The method of claim 21, wherein the presence of hetero-aggregates of the antibody or antibody fragment and the contaminant is substantially eliminated.

25. The method of claim 1, wherein the antibody or antibody fragment is a recombinant protein.

26. The method of claim 1, wherein the sample is a cell culture harvest, a cell culture supernatant, an antibody-containing solution derived from a cell culture, or an antibody-containing solution from a previous stage of protein purification.

27. The method of claim 26, wherein the cell culture comprises mammalian cells, bacterial cells, or yeast cells.

28. The method of claim 26, wherein the sample is an antibody-containing solution from a previous stage of protein purification.

29. The method of claim 1, wherein the sample is an eluate from a chromatography column.

30. The method of claim 1, wherein the sample is unpurified, is highly purified, or is in a range of about 40% to about 90% purity.

31. The method of claim 1, wherein the supernatant is contacted with the first and second components by flowing the supernatant through the first and second components.

32. The method of claim 1, wherein the electronegativity of the surface of the first component is conferred through one or more kinds of complex chemical moieties that embody more than one chemical functionality, or through a combination of simple and complex chemical groups mixed on the surface, or a combination of surfaces of differing chemical composition.

33. The method of claim 1, wherein the electropositivity of the surface of the second component is conferred through one or more kinds of complex chemical groups that embody more than one chemical functionality, or through a combination of simple and complex chemical groups mixed on the surface, or a combination of surfaces of differing chemical composition.

34. The method of claim 1, wherein the electronegativity of the surface of the first component is conferred in part by iminodiacetic acid and the electropositivity of the surface of the second component is conferred in part by tris(2-aminoethyl)amine.

35. The method of claim 1, wherein the first component has a surface-bound chemical moiety possessing metal affinity functionality.

36. The method of claim 1, wherein the electropositive surface of the second component includes a surface-bound chemical moiety possessing metal affinity functionality.

37. The method of claim 35 or 36, wherein at least one of the substrates has one or more chemical moieties in addition to the surface-bound chemical moiety possessing metal affinity functionality wherein such additional chemical moieties enhance the capacity of one or more of the components to participate in hydrogen bonding, hydrophobic interactions, or pi-pi binding with a protein of the protein preparation.

38. The method of claim 35 or 36, wherein the surface-bound chemical moiety possessing metal affinity functionality is a multidentate metal chelating moiety.

39. The method of claim 1, wherein the electropositive surface of the first component includes a surface-bound chemical moiety possessing metal affinity functionality, the electronegative surface of the second component includes a surface-bound chemical moiety possessing metal affinity functionality, and another surface includes a surface-bound chemical moiety possessing an elevated hydrophobic functionality.

40. The method of claim 2, wherein the organic multivalent cation of mixed chemical character is selected from the group consisting of ethacridine, 9-aminoacridine (aminacrine), 3,6 acridinediamine (proflavin), acrisorcin, acrizane (phenacridane), acridine orange, quinacrine, acricide, acridone, acridine-9-carboxylic acid, acranil (1-[(6-chloro-2-methoxy-9-acridinyl)amino]-3-(diethylamino)-2-propanol dihydrochloride), phenosafranin, phenoxazine, phenothiazine, acriflavine (3,6-diamino-10-methylacridinium, chloride and 3,6-acridineidiamine), polyethyleneimine, chlorhexidine, and poly-amino acids.

41. The method of claim 2, wherein the organic multivalent cation of mixed chemical character is ethacridine, polyethylenimine or chlorhexidine or a salt thereof.

42. The method of claim 2 wherein the organic multivalent cation of mixed chemical character is ethacridine or a salt thereof.

43. The method of claim 40, wherein the organic multivalent cation of mixed chemical character is present in an amount between approximately 0.01% and approximately 0.05%.

44. The method of claim 40, wherein the organic multivalent cation of mixed chemical character is present in an amount less than approximately 0.01%.

45. The method of claim 44, wherein the organic multivalent cation of mixed chemical character is present in an amount less than approximately 0.005%.

46. The method of claim 44, wherein the organic multivalent cation of mixed chemical character is present in an amount less than approximately 0.001%.

47. The method of claim 40, wherein the organic multivalent cation of mixed chemical character is present in an amount between approximately 0.020 and approximately 0.025%.

48. The method of claim 1, wherein the sample or supernatant is treated with more than one organic multivalent cation selected from the group consisting of polyethyleneimine, polyallyamine, ethacridine, and chlorhexidine and salts thereof prior to the step of contacting the supernatant with the first and second components.

49. The method of claim 48 wherein the organic multivalent cations are provided in a concentration of less than 1%.

50. The method of claim 48 wherein the organic multivalent cations are provided in a concentration between approximately 0.01% and approximately 0.05%.

51. The method of claim 48 wherein the organic multivalent cations are provided in a concentration less than approximately 0.01%.

52. The method of claim 51, wherein the organic multivalent cations are provided in a concentration less than approximately 0.005%.

53. The method of claim 51, wherein the organic multivalent cations are provided in a concentration less than approximately 0.001%.

54. The method of claim 48 wherein the organic multivalent cations are provided in a concentration between approximately 0.020 and approximately 0.025%.

55. The method of claim 1, wherein the sample or supernatant is additionally contacted with a soluble organic modulator selected from the group consisting of nonionic organic polymers, organic solvents, surfactants, and ureides, prior to the step of contacting the supernatant with the first and second components.

56. The method of claim 1, wherein the sample or supernatant is additionally contacted with an antiviral agent, prior to the step of contacting the supernatant with the first and second components.

57. The method of claim 56 wherein the antiviral agent is a non-multivalent organic cation.

58. The method of claim 56 wherein the antiviral agent is selected from the group consisting of benzalkonium chloride, methylene blue and tri (n-butyl) phosphate.

59. The method of claim 56, wherein the antiviral agent is present in an amount less than approximately 1% (w/v).

60. The method of claim 56 wherein the antiviral agent is present in an amount less than approximately 0.1% (w/v).

61. The method of claim 60 wherein the antiviral agent is present in an amount less than approximately 0.01% (w/v).

62. The method of claim 61 wherein the antiviral agent is present in an amount less than approximately 0.001% (w/v).

63. The method of claim 2, wherein the step of contacting the sample with the ureide occurs prior to contacting the sample or supernatant with the soluble organic multivalent cation of mixed chemical character.

64. The method of claim 2 wherein the step of contacting the sample with the ureide occurs substantially simultaneously with contacting the sample or supernatant with the soluble organic multivalent cation of mixed chemical character.

65. The method of claim 2 wherein the step of contacting the sample with the ureide occurs after contacting the sample with the soluble organic multivalent cation of mixed chemical character.

66. The method of claim 1, wherein the ureide is selected from the group consisting of urea, uric acid, hydantoin, allantoin, alcloxa, aldioxa, hemocane, ureidohydantoin, 5-ureidohydantoin, glyoxylureide, glyoxylic acid diureide, 2,5-dioxo-4-imidazolidinyl urea, and purines.

67. The method of claim 66 wherein the ureide is allantoin.

68. The method of claim 66 wherein the ureide is uric acid.

69. The method of claim 67 wherein the allantoin is present in an amount greater than 0.5% (w/v).

70. The method of claim of claim 69 wherein the allantoin is present in an amount greater than approximately 1% (w/v).

71. The method of claim 68 wherein the uric acid is present in an amount greater than 0.0025% (w/v).

72. The method of claim 70 wherein the allantoin is present in an amount greater than approximately 2% (w/v).

73. The method of claim 70 wherein the allantoin is present in an amount greater than approximately 5% (w/v).

74. The method of claim 70 wherein the allantoin is present in an amount greater than approximately 10% (w/v).

75. The method of claim 55, wherein the organic modulator is a nonionic organic polymer selected from the group consisting of glycerol, polyethylene glycol, polypropylene glycol and polybutylene glycol.

76. The method of claim 75 wherein the nonionic organic polymer has an average molecular weight of approximately 500 D or less.

77. The method of claim 55, wherein the organic modulator is an organic solvent selected from the group consisting of ethylene glycol, propylene glycol, butylene glycol, dimethylsulfoxide, ethanol, isopropanol, and phenoxyethanol.

78. The method of claim 77, wherein the organic modulator is provided at a concentration of approximately 1% (w/v) or greater.

79. The method of claim 55, wherein the organic modulator is a surfactant selected from the group consisting of Tween, triton, CHAPS, CHAPSO and octyl glucoside.

80. The method of claim 79 wherein the surfactant is provided at a concentration of approximately 1% (w/v) or less.

81. The method of claim 79 wherein the surfactant is provided at a concentration of approximately 0.1% (w/v) or less.

82. The method of claim 55, wherein the organic modulator is a ureide provided in a subsaturating amount.

83. The method of claim 82, wherein the ureide is selected from the group consisting of urea, hydantoin, and allantoin.

* * * * *